US011535860B2

(12) United States Patent
Yang et al.

(10) Patent No.: US 11,535,860 B2
(45) Date of Patent: Dec. 27, 2022

(54) GENES FOR ENHANCING SALT AND DROUGHT TOLERANCE IN PLANTS AND METHODS OF USE

(71) Applicant: UT-Battelle, LLC, Oak Ridge, TN (US)

(72) Inventors: Xiaohan Yang, Knoxville, TN (US); Degao Liu, Falcon Heights, MN (US); Rongbin Hu, Farragut, TN (US); Gerald A. Tuskan, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 16/774,552

(22) Filed: Jan. 28, 2020

(65) Prior Publication Data

US 2020/0239901 A1 Jul. 30, 2020

Related U.S. Application Data

(60) Provisional application No. 62/797,452, filed on Jan. 28, 2019.

(51) Int. Cl.
*C12N 15/82* (2006.01)
(52) U.S. Cl.
CPC .. *C12N 15/8273* (2013.01); *C12Y 401/01031* (2013.01)
(58) Field of Classification Search
None
See application file for complete search history.

(56) References Cited

U.S. PATENT DOCUMENTS

2003/0221218 A1  11/2003  Wilkins
2018/0371487 A1  12/2018  Yang et al.

OTHER PUBLICATIONS

Abdolreza et al. "Structures of Phosphoenolpyruvate carboxylase (PEPC) Gene Promoter from C4 and C3 Flaveria species Using Sequence Analysis by Bioinformatics Tools". Annual Research & Review in Biology. 4(17): 2779-2794 (Year: 2014).*
Stockhaus et al. "The Promoter of the Gene Encoding the C4 Form of Phosphoenolpyruvate Carboxylase Directs Mesophyll-Specific Expression in Transgenic C4 Flaveria spp". The Plant Cell, vol. 9, 479-489. (Year: 1997).*
Yang, et al. "Leveraging Agave and Kalanchoë Genomics Resources to Transfer Crassulacean Acid Metabolism (CAM) Modules into C3 Species Using Synthetic Biology Approaches" (Year: 2017).*

(Continued)

*Primary Examiner* — Matthew R Keogh
*Assistant Examiner* — David R Byrnes
(74) *Attorney, Agent, or Firm* — Scully, Scott, Murphy & Presser, P.C.

(57) ABSTRACT

The present disclosure provides methods for increasing drought resistance, salt resistance, photosynthetic rate, biomass production and water-use efficiency of a plant. The methods encompass expression of CAM-specific a phosphoenolpyruvate carboxylase (PEPC) in the plant. In comparison to a plant not manipulated in this manner, the disclosed, genetically-modified, plants display improved drought resistance and salt resistance. Also provided are plants that can be obtained by the method according to the invention, and nucleic acid vectors to be used in the described methods.

24 Claims, 18 Drawing Sheets
(15 of 18 Drawing Sheet(s) Filed in Color)
Specification includes a Sequence Listing.

(56) References Cited

OTHER PUBLICATIONS

Davis, et al. "Productivity and water use efficiency of Agave americana in the first field trial as bioenergy feedstock on arid lands". GCB Bioenergy. 9: 314-325. (Year: 2017).*
Hudspeth, et al. "Expression of Maize Phosphoenolpyruvate Carboxylase in Transgenic Tobacco" Plant Physiology. 98: 458-464. (Year: 1992).*
Kogami et al. "Molecular and physiological evaluation of transgenic tobacco plants expressing a maize phosphoenolpyruvate carboxylase gene under the control of the cauliflower mosaic virus 35S promoter". Transgenic research. 3: 287-296. (Year: 1994).*
Davis et al. "Light to liquid fuel: theoretical and realized energy conversion efficiency of plants using Crassulacean Acid Metabolism (CAM) in arid conditions". Journal of Experimental Botany. 65 (13): 3471-3478 (Year: 2014).*
Borland, et al. "Engineering crassulacean acid metabolism to improve water-use efficiency". Trends in Plant Science. 19(5): 327-338. (Year: 2014).*
Genbank Accession No. D83052.1 (2 pages) (Sep. 15, 2007).
International Search Report and Written Opinion dated Apr. 27, 2020 received in International Application No. PCT/US20/15389.
Abraham, P.E, et al., "Transcript, protein and metabolite temporal dynamics in the CAM plant Agave",Nature Plants, article No. 16178, pp. 1-45 (Nov. 21, 2016).
Borland, A.M. et al., "Engineering crassulacean acid metabolism to improve water-use efficiency", Trends in Plant Science, vol. 19, No. 5, pp. 327-338 (May 2014).
Hurst, A. et al., "Effects of salinity, high irradiance, ozone, and ethylene on mode of photosynthesis, oxidative stress and oxidative damage in the C3/CAM intermediate plant *Mesembryanthemum crystallinum* L.", Plant, Cell & Environment 27: 187-197 (2004).
Liu, D. et al., "Overexpression of IbP5CR enhances salt tolerance in transgenic sweetpotato", Plant Cell, Tissue and Organ Culture (PCTOC) 117:1-16.
Luttge, U., "The role of crassulacean acid metabolism (CAM) in the adaptation of plants to salinity*", New Phytol., vol. 125, pp. 59-71 (1993).
Owen, N.A. et al., "A system dynamics model integrating physiology and biochemical regulation predicts extent of crassulacean acid metabolism (CAM) phases", New Phytologist 200: 1116-1131 (2013).
Singh, V.J. et al., A novel transcription factor-like gene SbSDR1 acts as a molecular switch and confers salt and osmotic endurance to transgenic tobacco, Scientific Reports 6: 31686 (2016).
Yang, X. et al., "A roadmap for research on crassulacean acid metabolism (CAM) to enchance sustainable food and bioenergy production in a hotter, drier world", New Phytol., vol. 207, pp. 491-504 (2015).
Yang, X. et al., The Kalanchoe genome provides insights into convergent evolution and building blocks of crassulacean acid metabolism, Nature Communications, 8: 1899, pp. 1-15 (2017).

* cited by examiner

A

15th days without watering

WT　　EV　　OE1　　OE2

3th day after re-irrigation

WT　　EV　　OE1　　OE2

SEQUENCE LISTING

```
<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: oligonucleotide

<400> SEQUENCE: 1
gcctacagga ggaggagtac gctg                                          24

<210> SEQ ID NO 2
<211> LENGTH: 24
```

```
<212> TYPE: DNA
<213> ORGANISM: Artificial Sequence
<220> FEATURE:
<223> OTHER INFORMATION: oligonucleotide

<400> SEQUENCE: 2
cctgactgac tgagtcggat gtgc                                           24

<210> SEQ ID NO 3
<211> LENGTH: 22
<212> TYPE: DNA
<213> ORGANISM: Artificial Sequence
<220> FEATURE:
<223> OTHER INFORMATION: oligonucleotide

<400> SEQUENCE: 3
aatggttcag agtatggatt gg                                             22

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
taagtgtcgc acctatgctg                                                20

<210> SEQ ID NO 5
<211> LENGTH: 22
<212> TYPE: DNA
<213> ORGANISM: Artificial Sequence
<220> FEATURE:
<223> OTHER INFORMATION: oligonucleotide

<400> SEQUENCE: 5
gtcaaagccc taagttcttg gt                                             22

<210> SEQ ID NO 6
<211> LENGTH: 24
<212> TYPE: DNA
<213> ORGANISM: Artificial Sequence
<220> FEATURE:
<223> OTHER INFORMATION: oligonucleotide

<400> SEQUENCE: 6
acccactctt caatgaaatc actg                                           24

<210> SEQ ID NO 7
<211> LENGTH: 21
<212> TYPE: DNA
<213> ORGANISM: Artificial Sequence
<220> FEATURE:
<223> OTHER INFORMATION: oligonucleotide

<400> SEQUENCE: 7
ttggatatgc tcttgttccg a                                              21

<210> SEQ ID NO 8
<211> LENGTH: 22
<212> TYPE: DNA
<213> ORGANISM: Artificial Sequence
<220> FEATURE:
<223> OTHER INFORMATION: oligonucleotide

<400> SEQUENCE: 8
```

```
gcaacaacac ctttgagaag ag                                                    22

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
tggcttgtgg attcaaaggg                                                       20

<210> SEQ ID NO 10
<211> LENGTH: 23
<212> TYPE: DNA
<213> ORGANISM: Artificial Sequence
<220> FEATURE:
<223> OTHER INFORMATION: oligonucleotide

<400> SEQUENCE: 10
ggttggctta atggtcttaa cag                                                   23

<210> SEQ ID NO 11
<211> LENGTH: 24
<212> TYPE: DNA
<213> ORGANISM: Artificial Sequence
<220> FEATURE:
<223> OTHER INFORMATION: oligonucleotide

<400> SEQUENCE: 11
taatactcag gtggttgaag acag                                                  24

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
caaagtaaag acagtggcgg                                                       20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
cttcaggcac tttcttccca                                                       20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
catcagcaac ctccgttctc                                                       20

<210> SEQ ID NO 15
<211> LENGTH: 23
<212> TYPE: DNA
<213> ORGANISM: Artificial Sequence
```

```
<220> FEATURE:
<223> OTHER INFORMATION: oligonucleotide

<400> SEQUENCE: 15
tggaactgtt agtgtcatga tgg                                          23

<210> SEQ ID NO 16
<211> LENGTH: 22
<212> TYPE: DNA
<213> ORGANISM: Artificial Sequence
<220> FEATURE:
<223> OTHER INFORMATION: oligonucleotide

<400> SEQUENCE: 16
ctggtgcaat ggctaagtat gg                                           22

<210> SEQ ID NO 17
<211> LENGTH: 5044
<212> TYPE: DNA
<213> ORGANISM: Agave americana

<400> SEQUENCE: 17
ggcagctccc ttcttcgata aaatttgaaa tgtttatata ttttacatgg ggttgaactg    60
tctgaataag tctataattt cactttcatc ggttgttgcg agtctatctt acacacctta   120
tgaacaaagt taaatcaccg ctcttggaaa aataagataa aaattccacc tctcagttca   180
gagtggagag agagtggatg gtacttgagt cagcttctga atctcctcca caaacctctc   240
catcgcaggc ccggaagcaa acaggcacaa caatcccatc ccggaagcgt atgtaaaagc   300
taaccaggtc ctgaatcgca tccactggcc catcgtacac cgccttcccc cacccgaagt   360
ccacgtcacc ggtcccggcc ggtcacgtcc gacacaacgt gcgaccgcac caaggtgaag   420
tggggccgcc ctctgagcac catcagatcc gccaccgacc tcatgtactc ctccgtcacc   480
gcggccttgg cctccttcac cagcccaggc gtaccccaac gggttccgcg cagcctgtc    540 cgccctcgac accgccacgg ggaacgcaat cacgttgccg tagaatcccc gaggcagcgg   600
ggggtcgaac ttgttccggg cgttgacgac gagatatgcg cacctcctcg tccgggtcgg   660
gacgcagcgc gatggtccgg cacttccaga ggcaggcggt cagcacctcg aaggtggagc   720
tgggacgcat gtgaggggc acttgcttct tcagtgagct attctttggg tccgaagaag   780
aaggagcggt ggatcatgtc gtcgagggtg ccatccgtgt ccgggaccac gtcgtactct   840
cggtgcacgc aggttgggtt cgggggggttt ctcgcgtcga ggactcccgt tccagacggg   900
cgggaccgtg ggggcttgca ggccgcgtgc catctcgctg acggcgttca agaatagggc   960
gagtcctggg gcgtcggcca tcgtgtggtt gaggaggagg gcgaagatga gccgcccaga  1020
gcaggcgagt cacctgtttg ttactcactg agtgcaatcg agcaagtaaa acacaaagtt  1080
tagttagtca cctgaatcag gaggagtggg caattgagga tctctccgga cccttagcat  1140
caacagcagc tcctcgatgc acgggaacgg aggcagcagc tcctccccaa actgctccag  1200
acgaacatcg gcgtccgcct cgatgaacaa cactccctcg ccgctgcact ccaccaacag  1260
ctccggtccg tcctaattcc ctcagcctgc cggcgaacgg gtagtaaaac acaagggcct  1320
tcgccagggc ccttttgatg accgcaacgg gatcgcgtcc tctcacctct gacttgcgac  1380
ccccgcgtcc tgcctgctct cacgggcttc tcttcactct tcatctcctt tcctgagaaa  1440
atagcagaaa gattttctaa ggtatcgtgt tcgagttgat ataagcagct cgggtttgag  1500
gaagagacga gagctgttgt tggggagaag cagagatgac tcgagtggag aagttagcgt  1560
```

```
cggttgatgc gcagctgagg cttttggcgc cggcgaaagt gtcggaggat gacaaattgg    1620
tggagtacgt tgcgatgctt tggatcggtt ctcgatatac tccaagattt gcacggggga    1680
gaaattagag agacggttca agagtgctat gagctatctg ctgagtacga gggaaagcat    1740
gatcccaaga agttagagga actgggaatg tgctgacggt tttggatcccg gggattccat    1800 tgtggttgcc agctcgttct cgcacatgct caacttggct aacttggccg aggaggtaca    1860
aattgcctac aggaggagga gtacgctgaa gagaagggtg attttttgat gaggcctctg    1920
caactactga atcagacctt gaagagacct ttaaaaggct tattgtgcag ttgaaaaagt    1980
ctccggagga gattttttgat gctttgaaga accaaacgtc gatctggttt ttctgcacat    2040
ccgactcagt cagtcaggag gtcgctgctt cagaagcacg gaaggataag gaattgctta    2100
gcgcagctgt gtgccaaaga tatatcacct aatgataagc agggcttgat gaggctctca    2160
gagagagatt caagctgcct ttagaactga tgaaatccga agaacacctc ccactccaca    2220
agatgaaatg aggaccggaa tgagttattt ccatgaaacc atatggaatg tgttcccaag    2280
ttcttagtcg tgttgacaca gcgctgaaaa acattggcat caatgagcgt tttccataca    2340
atgctcctct tattcaattt tcttcttgga tggggggtga tcgtgatgga aatccagagt    2400
gactccagaa gtacaaggga cgtgtgcctg ttagcaagaa tgatggctgc aaacttgtac    2460
ttttcccaga ttgaagattt aatgtttgag ctatcaatgt ggcgctgcag tgaggagcta    2520
ctgtccaagc agataaacta attccacatc aaagaaggat gcaaaacatt ttatagagtt    2580
ttggaaacaa attcctctaa atgagcctta ccgtgttata cttggtggtg tgagagataa    2640
gctatatata ctcgagagag aacacggagt tattgtcaaa tgggtactct gacattcctg    2700
aggaagcaac tttcaccaat gctgagcagt tcctggaacc ccttgaatta tgctaccggt    2760
cgctctgtgc ttgggtgata gacccatagc tgatgaagcc ttctggactt tttgcgccaa    2820
gtatcaacct ttggcctgtc tcttgtgaaa cttgacatca ggcaagaatc tgaaaggcac    2880
actgatgtta tggatgccac accaggcatc tagaaattgg tcctatcgtg agtggtctga    2940
ggagaagcgt caggaatggt tgttgtctga acttagtgga aaacgtccgc tgtttggtcc    3000
tgatcttccg aaaactgaag aaatcatgat gttctagaaa cgttccattc attgcggatc    3060
tgccttccga tagctttgga gcgtacgtca tctcaatggc aacttctaca tctgatgttc    3120
ttgctgtcga actcttgcag cgagcatacc ggtgaagaat ccattgagag ttgtgctcta    3180
tttgagaaac ttgcagacct tgagacagcg cctgctgctg tagaaagact cttcgcaata    3240
gactggtaca ggaacaggat caatggaaag caagaagtat gattggatac tcagattctg    3300
ggaggatgct ggacgccttt ctgcaggttg gcagttatat aaagctcaag aagacctagt    3360
aaaggttgcc cagaaatatg gtgtaaagtt gacaatgttc catgacgagg gggtactgtt    3420
gggagaggag gcggtcctac tcatcttgct atactctctc agccaccaga cacaatccgt    3480
gggtcacttc gtgttacagt ccagggtgaa gttattgaac agtctttcgg cgaagagcgt    3540
ttgtttcaaa acactccaac gtttcacagc tgctactctt gagcatggga tgcgtcctcc    3600
gatttctcca aagccagaat ggcgtgcttt gatggatgag atggctgttg tggccacgaa    3660
agaataccga cttcgtcttt cagcaaccac ggtttgttga gtacttccgc ctggcaacac    3720
ctgagacaga atacggtcgg atgaacattg gcagtcggcc atcaaaacgg aagcccagtg    3780
ggggcataga gtcattcggc aattccatgg atattcgcat ggactcaaac aaggtttcac    3840
cttccagtgt ggcttggctt tggtgcagca ttcaagtttg tcatgaaaaa ggatatcaag    3900
agtctacaaa ctctacaaga gagtaaaggg gtggccattc ttcagggtca ccattgactt    3960
```

```
gattgagatg gttttttgcaa agggagatcc tgtaatagct gctttatatg ataagcttct    4020
agtttctgaa gagttgcagc cgcttgggag cattaagagc caattatgaa gaaacagagc    4080
gtctccttct gcaggttgct ggtaaccaag atcttcttga aggggatcca ttcttgaagc    4140
agagactgcg cctccgtcgt tcttacataa caagctgcag tgtgccaagc ctacaccctg    4200
aagcgaatca gagatcctga ttacaacgta caactgaggc cccgcctgtc gaaggaggtc    4260
atggagtctc ataaagctgc tgaagaactg gtgaagctaa ccccacagcg agtacgcgcc    4320
agggttagaa gacacattga tcattaccat gaagggaata gctgcaggcc tgcaaaacac    4380
tggttgaact catctggtta tatacatatg gagcctagca tatataatat ttgatctatt    4440
tccggaactt tttgcatatt ggactagaaa catggcggct ggcaccatgc tttgtattta    4500
cttgtactta tgcagactga gcgacaggct cttttagaat aaactacgcg agtcgcgtat    4560
tctcttgttg taattgcaaa tatctcttgt tgtaattgca agggaagtct ggttctgaat    4620
ttgcagtgat gctactgttg ttagaactgg ttgctgaagt gatattgcat taccttgacg    4680
tgtactcgtt ttgtgctaga gatggacata ttatgtgccc acttgaaaaa tatgagtaac    4740
ttgcatcagt tttgtgctca ataggaatca cgtatgcgtt tcacagttca tatttaaagc    4800
ggcccgccct gcatatttgt gagggagtcg ggctaaaaga gtccggatct ggggctccta    4860
ggtttgactc cgactcattg tcatccctca acgaaggtca agcttgtgtg gaccgaggat    4920
tgtggacctg gatgcaaact cagcccatgg gcctcgatcg aggttcgccc caagtgagaa    4980
ggacctcctg ggcttattgt gggaactgat cttcaaagtt cgtcgggagc tcgctcaatt    5040
gggc                                                                 5044

<210> SEQ ID NO 18
<211> LENGTH: 2851
<212> TYPE: DNA
<213> ORGANISM: Agave americana

<400> SEQUENCE: 18
atgactcgag tggagaagtt agcgtcggtt gatgcgcagc tgaggctttt ggcgccggcg     60
aaagtgtcgg aggatgacaa attggtggag tacgttgcga tgctcttgga tcggttcctc    120
gatataccaa gatttgcacg ggggagaaat tagagagacg gttcaagagt gctatgagct    180
atctgctgag tacgagggaa agcatgatcc caagaagtta gaggaactgg ggaatgtgct    240
gacgagtttg gatcggggat tccattgtgg ttgccagctc gttctcgcac atgctcaact    300
tggctaactt ggccgaggag gtacaaattg cctacaggag gaggagtacg ctgaagaaga    360
agggtgattt tgttgatgag ctctgcaact actgaatcag accttgaaga gacctttaaa    420
aggcttattg tgcagttgaa aaagtctccg gaggagattt tgatgctttt gaagaaccaa    480
acagtcgatc tggttttttac tgcactccac tcagtcagtc aggaggtcgc tgcttcagaa    540
gcacggaagg ataaggaatt gcttagcgca gctgtgtgcc aaagatatat cacctaatga    600
taagcaggag cttgatgagg ctctccagag aagatcaagc tgcctttaga actgatgaaa    660
tccgaagaac acctcccact ccacaagatg aaatgaggac cggaatgagt tatttccatg    720
aaaccatatg gaatggtgtt cccaagttct tacgtcggtt gaacagcgct gaaaacatt     780 ggcatcaatg agcgttttcc atacaatgct cctcttattc aattttcttc ttggatgggg    840
ggtgatcgtg atggaaatcc tagagtgact ccagaagtaa caaggacgtt gcctgttagc    900
aagaatgatg gctgcaaact tgtacttttc ccagattgaa gatttaatgt ttgagctatc    960
```

-continued

```
aatgtggcgc tgcagtgagg agctacgtgt ccaagcagat aaactacatc cacatcaaga    1020
aggatgcaaa acattttata gagttttgga aacaaattcc tctaaatgag ccttaccgtg    1080
ttatacttgg tggtgtgaga gataagctat attatactcg agagagaaca cggcattatt    1140
gtcaatgggt actctgacat tcctgaggaa gcaactttca ccaatgctga gcagttcctg    1200
gaaccccttg aattatgcta ccggtcgctc tgtgcttgtg gtgatagacc catagctgat    1260
gaagccttct gacttttgc gccaagtatc aacctttggc ctgtctcttg tgaaacttga    1320
catcaggcaa gaatctgaaa ggcacactga tgttatggat gccatcacca ggcatctaga    1380
aattggtcct atcgtgatgg tctgaggaga agcgtcagga atggttgttg tctgaactta    1440
gtggaaaacg tccgctgttt ggtcctgatc ttccgaaaac tgaagaaatc aatgatgttc    1500
tagaaacgtt ccagtcattg cggactgcct tccgatagct ttggagcgta cgtcatctca    1560
atggcaactt ctacatctga tgttcttgct gtcgaactct gcagcgagc ataccgtgtg     1620 aagaatccat tgagagttgg cctctatttg aaaacttgca gaccttgaga cagcgcctgc    1680
tgctgtagaa agactcttcg caatagactg gtacaggaac aggatcaatg gaaagcaaga    1740
agttatgatt ggatactcag attctggaag gatgctggcg cctttctgca ggttggcagt    1800
tatataaagc tcaagaagac ctagtaaagg ttgcccagaa atatggtgta agttgacaa     1860 tgttccatgg acgaggggt actgttggga gggaggcggt cctaccatct gctatactc      1920 tctcagccac cagacacaat ccgtgggtca cttcgtgtta cagtccaggg tgaagttatt    1980
gaacagtctt tcggcgaaga gcgtttgtgc ttcaaaacac tccaacgttt cacagctgct    2040
actcttgagc atgggatgcg tcccgatttc tccaaagcca gaatggcgtg ctttgatgga    2100
tgagatggct gttgtggcca cgaaagaata ccgatcattc gtctttcagc aaccacggtt    2160
tgttgagtac ttccgcctgg caacacctgg cagaatacgg tcggatgaac attggcagtc    2220
ggccatcaaa acggaagccc agtggggca tagagtcatt acgtgcaatt ccatggatat     2280
tcgcatggac tcaaacaagg tttcaccttc cagtgggttg gctttggtgc agcattcaag    2340
tttgtcatgg aaaaggatat caagagtcta caaactctac aagagatgta aggggtgg      2400 ccattcttca gggtcaccat tgacttgatt gagatggttt tgcaagggag atcctgtaat    2460
agctgcttta tatgataagc ttctagtttc tgaagagttg cagccgcttg ggcagcagtt    2520
aagagccaat tatgaagaaa cagagcgtct ccttctgcag gttgctgtaa caagatcttc    2580
ttgaagggga tccattcttg aagcagagac tgcgcctccg tcgttcttac ataacaagtc    2640
tgcatgtgtg ccaagcctac accctgaagc gaatcagaga tcctgattac aactacaatg    2700 aggcccccgcc tgtcgaagga ggtcatggag tctcataaag ctgctgaaga actggtgaag    2760
ctaaacccca ccagcgagta cgcgccaggg ttagaagaca cattgatcat taccatgaag    2820
gaatactgca ggcctgcaaa acactggttg a                                    2851
```

<210> SEQ ID NO 19
<211> LENGTH: 950
<212> TYPE: PRT
<213> ORGANISM: Agave americana

<400> SEQUENCE: 19

```
Met Thr Arg Val Glu Lys Leu Ala Ser Val Asp Ala Gln Leu Arg Leu
 1               5                  10                  15

Leu Ala Pro Ala Lys Val Ser Glu Asp Lys Leu Val Glu Tyr Val
            20                  25                  30

Ala Met Leu Leu Asp Arg Phe Leu Asp Ile Leu Gln Asp Leu His Gly
```

```
            35                  40                  45
Gly Glu Ile Arg Glu Thr Val Gln Glu Cys Tyr Glu Leu Ser Ala Glu
 50                  55                  60

Tyr Glu Gly Lys His Asp Pro Lys Leu Glu Leu Gly Asn Val
 65                  70                  75                  80

Leu Thr Ser Leu Asp Pro Gly Asp Ser Ile Val Ala Ser Ser Phe
                     85                  90                  95

Ser His Met Leu Asn Leu Ala Asn Leu Ala Glu Glu Val Gln Ile Ala
                100                 105                 110

Tyr Arg Arg Arg Ser Thr Leu Lys Lys Gly Asp Phe Val Asp Ser
                115                 120                 125

Ala Thr Thr Glu Ser Asp Leu Glu Thr Phe Lys Arg Leu Ile Val
    130                 135                 140

Gln Leu Lys Lys Ser Pro Glu Glu Ile Phe Asp Ala Leu Lys Asn Gln
145                 150                 155                 160

Thr Val Asp Leu Val Phe Thr Ala His Pro Thr Gln Ser Val Arg Arg
                165                 170                 175

Ser Leu Leu Gln Lys His Gly Arg Ile Arg Asn Cys Leu Ala Gln Leu
                180                 185                 190

Cys Ala Lys Asp Ile Ser Pro Asn Asp Lys Gln Glu Leu Asp Glu Ala
                195                 200                 205

Leu Gln Arg Glu Ile Gln Ala Ala Phe Arg Thr Asp Glu Ile Arg Arg
    210                 215                 220

Thr Pro Pro Thr Pro Gln Asp Glu Met Arg Thr Gly Met Ser Tyr Phe
225                 230                 235                 240

His Glu Thr Ile Trp Asn Gly Val Pro Lys Phe Leu Arg Val Thr Ala
                245                 250                 255

Leu Lys Asn Ile Gly Ile Asn Glu Arg Phe Pro Tyr Asn Ala Pro Leu
                260                 265                 270

Ile Gln Phe Ser Ser Trp Met Gly Gly Asp Arg Asp Gly Asn Pro Arg
                275                 280                 285

Val Thr Pro Glu Val Thr Arg Asp Val Cys Leu Leu Ala Arg Met Met
    290                 295                 300

Ala Ala Asn Leu Tyr Phe Ser Gln Ile Glu Asp Leu Met Phe Glu Leu
305                 310                 315                 320

Ser Met Trp Arg Cys Ser Glu Glu Leu Arg Val Gln Ala Asp Lys Leu
                325                 330                 335

His Ser Thr Ser Lys Lys Asp Ala Lys His Phe Ile Glu Phe Trp Lys
                340                 345                 350

Gln Ile Pro Leu Asn Glu Pro Tyr Arg Val Ile Leu Gly Gly Val Arg
                355                 360                 365

Asp Lys Leu Tyr Tyr Thr Arg Glu Arg Thr Arg Leu Leu Asn Gly Tyr
    370                 375                 380

Ser Asp Ile Pro Glu Glu Ala Thr Phe Thr Asn Ala Glu Gln Phe Leu
385                 390                 395                 400

Glu Pro Leu Glu Leu Cys Tyr Arg Ser Leu Cys Ala Cys Gly Asp Arg
                405                 410                 415

Pro Ile Ala Asp Gly Ser Leu Leu Asp Phe Leu Arg Gln Val Ser Thr
                420                 425                 430

Phe Gly Leu Ser Leu Val Lys Leu Asp Ile Arg Gln Glu Ser Glu Arg
                435                 440                 445

His Thr Asp Val Met Asp Ala Ile Thr Arg His Leu Glu Ile Gly Ser
    450                 455                 460
```

```
Tyr Arg Glu Trp Ser Glu Glu Lys Arg Gln Glu Trp Leu Leu Ser Glu
465                 470                 475                 480

Leu Ser Gly Lys Arg Pro Leu Phe Gly Pro Asp Leu Pro Lys Thr Glu
            485                 490                 495

Glu Ile Asn Asp Val Leu Glu Thr Phe Val Ile Ala Leu Pro Ser Asp
                500                 505                 510

Ser Phe Gly Ala Tyr Val Ile Ser Met Ala Thr Ser Thr Ser Asp Val
            515                 520                 525

Leu Ala Val Glu Leu Leu Gln Arg Ala Tyr Arg Val Lys Asn Pro Leu
530                 535                 540

Arg Val Val Pro Leu Phe Glu Lys Leu Ala Asp Leu Glu Thr Ala Pro
545                 550                 555                 560

Ala Ala Val Glu Arg Leu Phe Ala Ile Asp Trp Tyr Arg Asn Arg Ile
                565                 570                 575

Asn Gly Lys Gln Glu Val Met Ile Gly Tyr Ser Asp Ser Gly Lys Asp
            580                 585                 590

Ala Gly Arg Leu Ser Ala Gly Trp Gln Leu Tyr Lys Ala Gln Glu Asp
            595                 600                 605

Leu Val Lys Val Ala Gln Lys Tyr Gly Val Lys Leu Thr Met Phe His
610                 615                 620

Gly Arg Gly Gly Thr Val Gly Gly Gly Pro His Leu Ala Ile Leu
625                 630                 635                 640

Ser Gln Pro Pro Asp Thr Ile Arg Gly Ser Leu Arg Val Thr Val Gln
                645                 650                 655

Gly Glu Val Ile Glu Gln Ser Phe Gly Glu Glu Arg Leu Cys Phe Lys
            660                 665                 670

Thr Leu Gln Arg Phe Thr Ala Ala Thr Leu Glu His Gly Met Arg Pro
            675                 680                 685

Pro Ile Ser Pro Lys Pro Glu Trp Arg Ala Leu Met Asp Glu Met Ala
690                 695                 700

Val Val Ala Thr Lys Glu Tyr Arg Ser Phe Val Phe Gln Gln Pro Arg
705                 710                 715                 720

Phe Val Glu Tyr Phe Arg Leu Ala Thr Pro Glu Thr Glu Tyr Gly Arg
                725                 730                 735

Met Asn Ile Gly Ser Arg Pro Ser Lys Arg Lys Pro Ser Gly Gly Ile
            740                 745                 750

Glu Ser Leu Arg Ala Pro Trp Ile Phe Ala Thr Gln Thr Arg Phe His
            755                 760                 765

Leu Pro Val Trp Leu Gly Phe Gly Ala Ala Phe Lys Phe Val Met Glu
            770                 775                 780

Lys Asp Ile Lys Ser Leu Gln Thr Leu Gln Glu Met Tyr Lys Gly Trp
785                 790                 795                 800

Pro Phe Phe Arg Val Thr Ile Asp Leu Ile Glu Met Val Phe Ala Lys
                805                 810                 815

Gly Asp Pro Val Ile Ala Ala Leu Tyr Asp Lys Leu Leu Val Ser Glu
            820                 825                 830

Glu Leu Gln Pro Leu Gly Gln Gln Leu Arg Ala Asn Tyr Glu Glu Thr
            835                 840                 845

Glu Arg Leu Leu Leu Gln Val Ala Gly Asn Gln Asp Leu Leu Glu Gly
            850                 855                 860

Asp Pro Phe Leu Lys Gln Arg Leu Arg Leu Arg Arg Ser Tyr Ile Thr
865                 870                 875                 880
```

-continued

```
Ser Leu His Cys Gln Ala Tyr Thr Leu Arg Ile Arg Asp Pro Asp Tyr
            885                 890                 895

Asn Val Gln Leu Arg Pro Arg Leu Ser Lys Glu Val Met Glu Ser His
            900                 905                 910

Lys Ala Ala Glu Glu Leu Val Lys Leu Asn Pro Thr Ser Glu Tyr Ala
            915                 920                 925

Pro Gly Leu Glu Asp Thr Leu Ile Ile Thr Met Lys Gly Ile Ala Ala
            930                 935                 940

Gly Leu Gln Asn Thr Gly
945                 950
```

GENES FOR ENHANCING SALT AND DROUGHT TOLERANCE IN PLANTS AND METHODS OF USE

CROSS REFERENCE TO RELATED APPLICATION

This application claims the benefit of priority of U.S. Provisional Application No. 62/797,452, filed Jan. 28, 2019, the entire contents of which are incorporated herein by reference.

STATEMENT REGARDING FEDERALLY SPONSORED RESEARCH OR DEVELOPMENT

This invention was made with government support under Prime Contract No. DE-AC05-00OR22725 awarded by the U.S. Department of Energy. The government has certain rights in the invention.

INCORPORATION BY REFERENCE OF SEQUENCE LISTING

The Sequence Listing in an ASCII text file, 37990_4140_1_SequenceListing.txt of 22 KB, created on Dec. 16, 2019, and submitted to the United States Patent and Trademark Office via EFS-Web, is incorporated herein by reference.

BACKGROUND

Human population growth, urbanization, global climate change, and reductions in natural resources could seriously impact future food and energy security (Yang X. et al. 2015. *New Phytologist*, 207: 491-504; Abraham P E. et al., 2016. *Nature Plants*, 2: 16178. 500; Yang X. et al. 2017. *Nature Communications*, 8: 1899). Approximately 40% of the world's land area is considered arid, semiarid, or dry sub-humid, with precipitation amounts that are inadequate for most present-day food and bioenergy crops which use $C_3$ or $C_4$ photosynthesis (Borland A M. et al., 2014. *Trends in Plant Science*, 19: 327-338). Also, around 19.5% of the irrigated soils in the world are under salt stress, and soil salinization has become a major constraint limiting crop production (Liu D. et al. 2014. *Plant Cell, Tissue and Organ Culture*, 117: 1-16). The development of crops with elevated levels of drought and salt tolerance, which could sustain production of food, feed, fiber, and biofuel on marginal land, is therefore highly desirable. Fortunately, a solution to these challenges exists in crassulacean acid metabolism (CAM), a specialized type of photosynthesis that enhances plant water-use efficiency (WUE) and associated drought avoidance/tolerance by shifting all or part of the $CO_2$ uptake to the nighttime, when evapotranspiration rates are reduced compared with the daytime (Borland A M. et al., 2014. *Trends in Plant Science*, 19: 327-338; Yang X. et al. 2015. *New Phytologist*, 207: 491-504). CAM is also evolved as an adaptation to salinized environments. Cacti having constitutive CAM show adaptation to salinity at the whole-plant level, engaging regulation of stomata, internal $CO_2$-recycling and root physiology with salt exclusion. The change from $C_3$- to CAM-photosynthesis in *Mesembryanthemum crystallinum* (common ice plant) is elicited by salinity. *M. crystallinum* plants, which are salt stress-tolerant with salt-induced responses at an array of levels: regulation of gas exchange, adjustments of metabolism, adaptation of transport protein and inductive changes of CAM gene expression (Lüttge U. 2002. *Journal of Experimental Botany*, 53: 2131-2142). Thus, engineering of CAM into $C_3$ or $C_4$ crops offers great potential for enhancing the sustainable production of food and biomass on semi-arid or marginal agricultural lands.

CAM photosynthesis can be divided into two major phases: Phase I takes place at night when the temperature is lower and humidity higher than during the day, with uptake of atmospheric $CO_2$ through open stomata and primary fixation of $CO_2$ by phosphoenolpyruvate carboxylase (PEPC) to oxaloacetate (OAA) and its subsequent conversion to malic acid by malate dehydrogenase; Phase II is defined as ribulose-1,5-bisphosphate arboxylase/oxygenase (RuBisCO) refixation of $CO_2$ released from malate decarboxylation by NAD(P)-malic enzyme (ME) or PEP carboxykinase (PEPCK) during daytime. As a key intermediate, malate accumulates throughout the night-time in the vacuole before being gradually degraded at daytime (Owen N A. et al. 2013. *New Phytologist* 200: 1116-1131; Yang X. et al. 2017. *Nature Communications* 8: 1899). Among all genes involved in Phase I, PEPC is the key enzyme for nocturnal $CO_2$ fixation. It has been shown that PEPC is a highly abundant enzyme in leaves of CAM plant and its expression level is an indicative of CAM plasticity.

SUMMARY OF THE DISCLOSURE

In one aspect, this disclosure provides a method of producing a $C_3$ or $C_4$ plant cell capable of producing a plant with improved drought and salt tolerance, photosynthetic rate, biomass production and water-use efficiency, comprising introducing into the plant cell a nucleic acid encoding a crassulacean acid metabolism (CAM)-specific phosphoenolpyruvate carboxylase (CAM-PEPC).

In some embodiments, the CAM-PEPC is an enzyme from a CAM plant selected from the group consisting of genera *Agave, Kalanchoe, Phalaenopsis, Ananas* and *Crassula*. In a specific embodiment, the CAM plant is *Agave americana*.

In some embodiments, the CAM-PEPC comprises an amino acid sequence substantially identical to SEQ ID NO: 19.

In some embodiments, the nucleic acid comprises a nucleic acid sequence substantially identical to SEQ ID NO: 18.

In some embodiments, the plant cell is from a $C_3$ plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia*, and *Triticum*.

In some embodiments, the plant cell is from a $C_4$ plant selected from the group consisting of genera *Panicum, Saccharum, Setaria, Sorghum* and *Zea*.

Another aspect of the disclosure is directed to a genetically modified plant cell produced by introducing into the plant cell a nucleic acid encoding a crassulacean acid metabolism (CAM)-specific phosphoenolpyruvate carboxylase (CAM-PEPC).

In some embodiments, the disclosure is directed to a plant generated from the genetically modified plant cell produced by introducing into the plant cell a nucleic acid encoding a crassulacean acid metabolism (CAM)-specific phosphoenolpyruvate carboxylase (CAM-PEPC).

In some aspects, the disclosure is directed to a genetically-modified $C_3$ or $C_4$ plant cell capable of producing a plant with improved drought and salt tolerance, photosynthetic rate, biomass production, and water-use efficiency, wherein the plant cell is modified to express a crassulacean acid metabolism (CAM)-specific phosphoenolpyruvate carboxylase (PEPC) (CAM-PEPC).

In some embodiments, the CAM-PEPC is an enzyme from a CAM plant selected from the group consisting of genera *Agave, Kalanchoe, Phalaenopsis, Ananas* and *Crassula*.

In some embodiments, the CAM plant is *Agave americana*.

In some embodiments, the CAM-PEPC comprises an amino acid sequence substantially identical to SEQ ID NO: 19.

In some embodiments, the nucleic acid comprises a nucleic acid sequence substantially identical to SEQ ID NO: 18.

In some embodiments, the plant cell is from a plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia, Triticum., Panicum, Saccharum, Setaria, Sorghum*, and *Zea*.

In another aspect, the disclosure is directed to an expression vector, comprising a nucleotide sequence operably linked to a regulatory region that is functional in a plant cell, wherein the nucleotide sequence encodes a crassulacean acid metabolism (CAM)-specific phosphoenolpyruvate carboxylase (CAM-PEPC).

In some embodiments, the CAM-PEPC is an enzyme from a CAM plant selected from the group consisting of genera *Agave, Kalanchoe, Phalaenopsis, Ananas* and *Crassula*.

In some embodiments, the CAM plant is *Agave americana*.

In some embodiments, the CAM-PEPC comprises an amino acid sequence substantially identical to SEQ ID NO: 19.

In some embodiments, the nucleic acid comprises a nucleic acid sequence substantially identical to SEQ ID NO: 18.

In some embodiments, the regulatory region comprises a promoter selected from the group consisting of a constitutive promoter, a tissue-specific promoter, and a regulated promoter.

In some embodiments, the tissue-specific promoter is a leaf-specific promoter.

In some embodiments, the leaf-specific promoter is selected from the group consisting of a ribulose-1,5-bisphosphate carboxylase/oxygenase (RbcS) promoter, a chlorophyll a/b binding-6 (cab6) promoter, a chlorophyll a/b binding-1(Cab-1) promoter, a cab IR promoter from rice, a pyruvate orthophosphate dikinase (PPDK) promoter, a light-harvesting complex of photosystem (Lhcb1*2) promoter, a sucrose-H+ symporter (SUC2) promoter and a thylakoid membrane protein promoter.

In some embodiments, the constitutive promoter is selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the regulated promoter is selected from the group consisting of a stress induced promoter, a chemical-induced promoter, a light induced promoter, a dark-induced promoter, and a circadian-clock controlled promoter.

In another aspect, the disclosure is directed to a method for improving drought and salt tolerance, photosynthetic rate, biomass production, and water-use efficiency in a plant cell, comprising introducing the expression vector comprising a nucleotide sequence operably linked to a regulatory region that is functional in a plant cell, wherein the nucleotide sequence encodes a crassulacean acid metabolism (CAM)-specific phosphoenolpyruvate carboxylase (CAM-PEPC), into a plant cell, and expressing the nucleotide sequence in the plant cell.

In another aspect, the disclosure is directed to a plant cell comprising the expression vector comprising a nucleotide sequence operably linked to a regulatory region that is functional in a plant cell, wherein the nucleotide sequence encodes a crassulacean acid metabolism (CAM)-specific phosphoenolpyruvate carboxylase (CAM-PEPC).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions

Figure 1A:
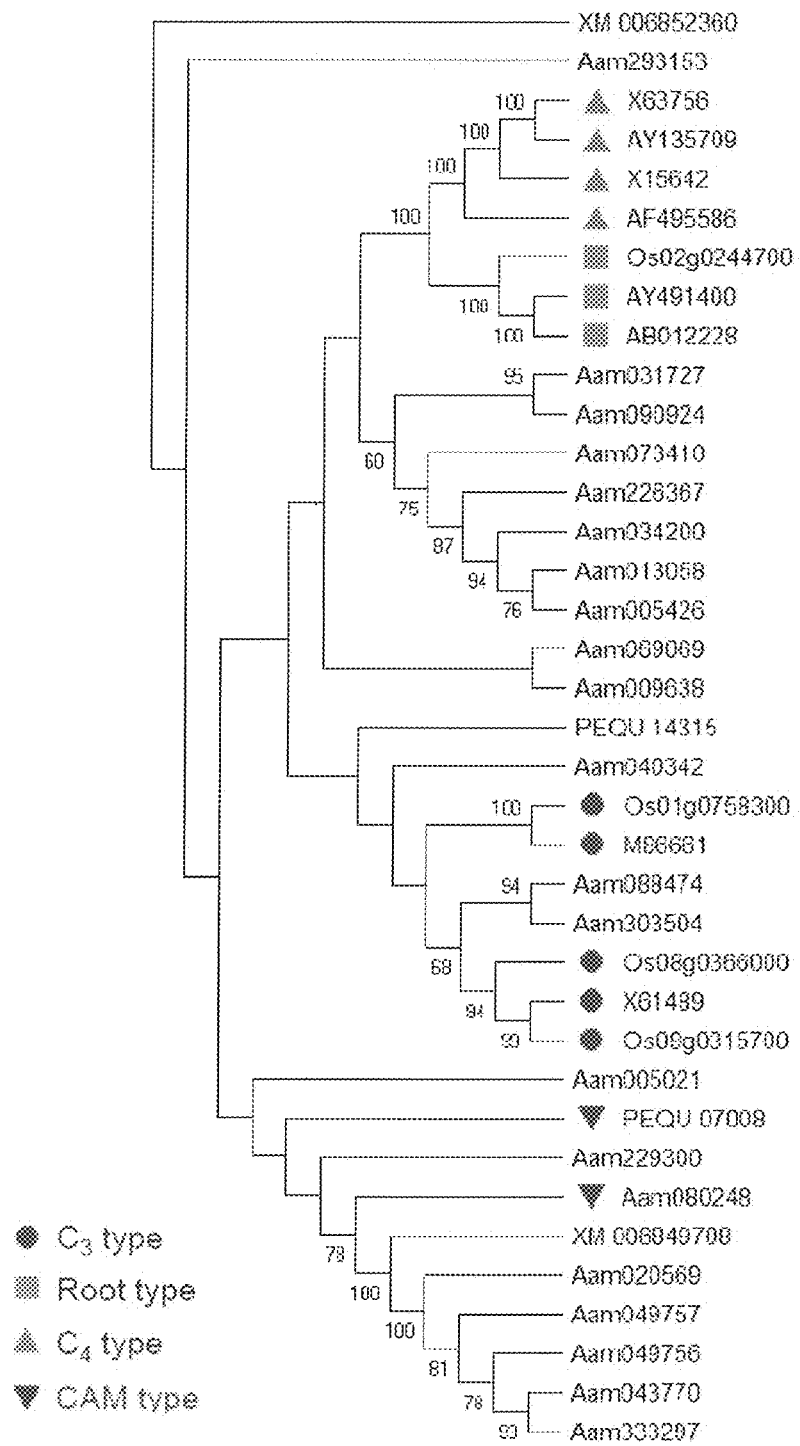
FIGS. 1A-1B. Identification of CAM-isoform of PEPC in *Agave americana*. (A) Phylogenetic relationships of PEPCs in *A. americana* and plant-type PEPCs from other monocot plants. Bootstrap values are shown at nodes. (B) Diel transcript expression of the PEPC genes in *A. Americana*. White and black bars indicate daytime (12-hour) and nighttime (12-hour), respectively.

Unless defined otherwise, all technical and scientific terms used herein have the same meaning as commonly understood by one of ordinary skill in the art to which this invention belongs.

As used herein, the term "about", when used in connection with a given value, refers to an approximately +/−10% variation from the given value.

The term "$C_3$ plant" refers to a plant that captures carbon dioxide into three-carbon compounds to enter into the Calvin cycle (photosynthesis pathway). In a $C_3$ plant carbon dioxide capture and the Calvin cycle occur during the daytime, and stomata of $C_3$ plants are open during the day for gas exchange, which also leads to increased water loss through the stomata (evapotranspiration).

The term "$C_4$ plant" refers to a plant that captures carbon dioxide into four-carbon compounds to enter into the Calvin cycle. In a $C_4$ plant carbon dioxide capture and the Calvin cycle occur during the daytime, and stomata of $C_4$ plants are open during the day for gas exchange, which also leads to increased water loss.

The term "crassulacean Acid Metabolism," also known as CAM, refers to a carbon fixation pathway that evolved in some plants as an adaptation to arid conditions. In a plant using full CAM, the stomata in the leaves remain shut during the day to reduce evapotranspiration, but open at night to collect carbon dioxide ($CO_2$). CAM plants include most succulents, such as cacti and agaves, as well as some orchids and bromeliads. Specific species of CAM plants include *Kalanchoe fedtschenkoi*, *Phalaenopsis equestris*, *Ananas comosus*, and *Crassula perforata*.

The term "control plant," as used herein, refers to a plant of the same species that does not comprise the modification or modifications described in this disclosure. In some embodiments, the control plant is of the same variety. In some embodiments, the control plant is of the same genetic background.

The term "DNA," as used herein, refers to a nucleic acid molecule of one or more nucleotides in length. By "nucleotide" it is meant a naturally-occurring nucleotide, as well modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

As used herein, the term "drought stress" or "drought" refers to a sub-optimal environmental condition associated with limited availability of water to a plant. Limited availability of water may occur when, for instance, rain is absent or lower and/or when the plants are watered less frequently than required. Limited water availability to a plant may also occur when for instance water is present in soil, but cannot efficiently be extracted by the plant. For instance, when soils strongly bind water or when the water has a high salt content, it may be more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states. Expression of a gene can be measured through a suitable assay, such as real-time quantitative reverse transcription polymerase chain reaction (qRT-PCR), Northern blot, transcriptome sequencing and Western blot.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically modified" (or "genetically engineered" or "transgenic" or "cisgenic") refers to a plant comprising a manipulated genome or nucleic acids. In some embodiments, the manipulation is the addition of exogenous nucleic acids to the plant. In some embodiments, the manipulation is changing the endogenous genes of the plant.

The term "homologous" refers to nucleic acids or polypeptides that are highly related at the level of nucleotide or amino acid sequence. Nucleic acids or polypeptides that are homologous to each other are termed "homologues." The term "homolog" refers to a gene related to a second gene by descent from a common ancestral DNA sequence, therefore, the corresponding polynucleotide/polypeptide has a certain degree of homology, that is to say sequence identity (preferably at least 50%, more preferably at least 60%, even more preferably at least 65%, particularly preferred at least 66%, 68%, 70%, 75%, 80%, 86%, 88%, 90%, 92%, 95%, 97% or 99%).

The term "improved drought resistance" (aka. "drought tolerance") refers to plants which, when provided with improved drought resistance, when subjected to drought or drought stress do not show effects or show alleviated effects as observed in control plants not provided with improved drought resistance. A normal plant has some level of drought resistance. It can easily be determined whether a plant has improved drought resistance by comparing a control plant with a plant provided with improved drought resistance under controlled conditions chosen such that in the control plants signs of drought can be observed after a certain period, i.e., when the plants are subjected to drought or drought stress. The plants with improved drought resistance will show less and/or reduced signs of having been subjected to drought, such as wilting, as compared to the control plants. The skilled person knows how to select suitable conditions. When a plant has "improved drought resistance," it is capable of sustaining normal growth and/or normal development when being subjected to drought or drought stress would otherwise have resulted in reduced growth and/or reduced development of normal plants. Hence, "improved drought resistance" is determined by comparing plants, whereby the plant most capable of sustaining (normal) growth under drought stress is a plant with "improved drought resistance." The skilled person is able to select appropriate conditions to determine drought resistance of a plant and how to measure signs of droughts, such as described in for example manuals by the IRRI, Breeding rice for drought prone environments, Fischer et al., 2003; and by the CIMMYT, Breeding for drought and nitrogen stress tolerance in maize: from theory to practice, Banzinger et al, 2000. Examples of methods for determining improved drought resistance in plants are provided in Snow and Tingey (Snow and Tingey, 1985, Plant Physiol, 77, 602-7) and Harb et al., Analysis of drought stress in Arabidopsis, AOP 2010, Plant Physiology Review.

The term "improved salt resistance" or "improved salt tolerance" refers to plants which, when provided with salt resistance (or being salt resistant), when subjected to high salt stress do not show effects or show alleviated effects as observed in plants not provided with salt resistance. When a plant is "salt resistant," it is capable of sustaining normal growth and/or normal development when being subjected to a high salt environment that otherwise would have resulted in reduced growth and/or development in normal plants. Hence, salt resistance is determined by comparing plants with another plant, whereby the plant most capable of sustaining (normal) growth may be a "salt resistant" plant, whereas the plant less capable may be termed a "salt sensitive" plant. Providing salt resistance thus is understood to include improving the salt resistance of a plant, when compared with a plant not provided with salt resistance. With plants provided with salt resistance it is e.g. possible to obtain higher yields of crop and/or plant product when the plant is subjected to a period or periods of high salt conditions when compared to plants not provided with salt resistance.

As used herein, the terms "*Kalanchoë laxiflora*" and "*Kalanchoë fedtschenkoi*" refer to the two CAM plant species from the genus *Kalanchoë*.

As used herein, the term "nucleic acid" has its general meaning in the art and refers to refers to a coding or non-coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e. nuclear or mitochondrial or chloroplast).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell*, 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

The term "substantially identical" refers to a sequence (nucleic acid or amino acid sequence) that is at least 80%, 85%, 88%, 90%, 95%, 98%, 99% or greater in sequence identity to a given reference sequence. The terms "substantial identity" or "substantially identical," as used herein, denote a characteristic of a polynucleotide or polypeptide sequence, wherein the polynucleotide or polypeptide comprises a sequence that has at least 80% sequence identity as compared to a reference sequence over the window of comparison allowing for gaps or mismatches of several bases, which may result from genetic mutation, polymorphism, evolutionary divergence or other phenomena. Polynucleotide or polypeptide sequences with at least 80%, 85%, 88%, 90%, 95%, 98% or 99% sequence identity as compared to a reference sequence over the window of comparison are also considered to have substantial identity with the reference sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

Plants

There is no specific limitation on the plants that can be used in the methods of the present disclosure, as long as the plant is suitable to be transformed by a gene. The term "plant," as used herein, includes whole plants, plant tissues or plant cells. The plants that can be used for the methods and compositions of the present disclosure include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus swinhoei Hance*, blackberry, bean, lentil, pea, soy, rape, mustard, opium poppy, olea europea, helianthus, coconut, plant producing castor oil, cacao, peanut, calabash, cucumber, watermelon, cotton, flax, cannabis, jute, citrus, lemon, grapefruit, spinach, lettuce, asparagus, cabbage, *Brassica campestris* L. ssp. *Pekinensis, Brassica campestris* L. ssp. chinensis, carrot, onion, murphy, tomato, green pepper, avocado, cassia, camphor, tobacco, nut, coffee, eggplant, sugar cane, tea, pepper, grapevine, nettle grass, banana, natural rubber tree and ornamental plant, etc.

In some embodiment the methods and compositions of the present disclosure are also be used over a broad range of plant species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, Oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In some embodiments, the plant for the methods and compositions of the present disclosure is a $C_3$ plant. In some embodiment, the $C_3$ plant is selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

In some embodiments, the plant for the methods and compositions of the present disclosure is a $C_4$ plant. In some embodiment, the $C_4$ plant is selected from the group consisting of genera *Panicum, Saccharum, Setaria, Sorghum* and *Zea*.

Methods of Improving Drought and Salt Tolerance Photosynthetic Rate, Biomass Production and Water-Use Efficiency in Plants The inventors of the present disclosure have described a process of improving drought and salt tolerance/resistance, photosynthetic rate, biomass production and water-use efficiency in plants. Drought tolerance/resistance and salt tolerance/resistance, increased photosynthetic rate, biomass production and water-use efficiency are desirable qualities that affect plant biomass. With methods of this disclosure, it is possible to generate engineered plants which produce more biomass, and/or more crop and plant product derived thereof, if grown under conditions of low water availability/drought in comparison with plants not subjected to the method according to the present disclosure. In some embodiments, the biomass of the engineered plant is increased by at least 5%, by at least 10%, by at least 15%, by at least 20%, by at least 25%, by at least 30%, by at least 40%, by at least 50%, or by at least 60% when compared to a corresponding control plant.

In some embodiments, the method comprises introducing into a plant an exogenous nucleic acid encoding a crassulacean acid metabolism (CAM)-specific phosphoenolpyruvate carboxylase (PEPC).

In some embodiments, the exogenous nucleic acid encodes a PEPC gene of a CAM plant species. In a specific embodiment, the CAM plant species is selected from the group consisting of genera *Agave, Kalanchoe, Phalaenopsis, Ananas* and *Crassula*. In a specific embodiment, the CAM plant species is selected from the group consisting of *Kalanchoe fedtschenkoi, Agave Americana, Phalaenopsis equestris* and *Ananas comosus*.

In a specific embodiment, the CAM plant species is *Agave americana*. In a specific embodiment, the CAM-specific PEPC comprises an amino acid sequence substantially identical with SEQ ID NO: 19, and a nucleic acid sequence substantially identical with SEQ ID NO: 18.

In some embodiments, the PEPC comprising is expressed constitutively. In some embodiments, the PEPC is expressed in a temporally controlled manner. In a specific embodiment, temporally controlled manner expression of PEPC refers to expression of the PEPC during night time.

In some embodiments a plant, plant cell or plant tissue can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Expression Vectors

The polynucleotides and expression vectors described herein can be used to increase the expression of a crassulacean acid metabolism (CAM)-specific phosphoenolpyruvate carboxylase (PEPC) in plants and render them drought and salt resistant.

In some embodiments, the vector comprises a nucleic acid sequence encoding for a PEPC enzyme from a CAM plant. In some embodiments, the PEPC is from a CAM plant species. In a specific embodiment, the CAM plant species is selected from the group consisting of *Kalanchoe fedtschenkoi, Phalaenopsis equestris* and *Ananas comosus*.

In a specific embodiment, the CAM plant species is *Agave Americana*. In a specific embodiment, the CAM-specific PEPC comprises an amino acid sequence substantially identical with SEQ ID NO: 19, and a nucleic acid sequence substantially identical with SEQ ID NO: 18.

The vectors provided herein can include origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione 5-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

In some embodiments, the promoter to drive expression of genes of interest is a constitutive promoter. In some embodiments the constitutive promoter is selected from the group consisting of a ubiquitin promoter, a cauliflower mosaic virus (CaMV) 35S promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the promoter to drive expression of genes of interest is a regulated promoter. In some embodiments the regulated promoter is selected from the group consisting of a stress induced promoter, chemical-induced promoter, a light induced promoter, a dark-induced promoter, and a circadian-clock controlled promoter.

Some suitable regulatory regions initiate transcription, only or predominantly, in certain cell types. For instance, promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine chlorophyll a/b binding-6 (cab6) promoter (Yamamoto et al., 1994, *Plant Cell Physiol.*, 35:773-778), the chlorophyll a/b binding-1 (Cab-1) promoter from wheat (Fejes et al., 1990, *Plant Mol. Biol.*, 15:921-932), the chlorophyll a/b binding-1 (CAB-1) promoter from spinach (Lubberstedt et al., 1994, *Plant Physiol.*, 104:997-1006), the cab IR promoter from rice (Luan et al., 1992, *Plant Cell*, 4:971-981), the pyruvate orthophosphate dikinase (PPDK) promoter from corn (Matsuoka et al., 1993. *Proc. Natl. Acad. Sci. USA*, 90:9586-9590), the tobacco light-harvesting complex of photosystem (Lhcb1*2) promoter (Cerdan et al., 1997, *Plant Mol. Biol.*, 33:245-255), the *Arabidopsis* SUC2 sucrose-H+ symporter promoter (Truernit et al., 1995, *Planta*, 196:564-570) and thylakoid membrane protein promoters from spinach (psaD, psaF, psaE, PC, FNR, atpC, atpD, cab, rbcS).

In some embodiments, promoters of the instant application comprise inducible promoters. Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863, incorporated herein by reference. If a cell or tissue culture is used as the recipient tissue for transformation, plants can be regenerated from transformed cultures if desired, by techniques known to those skilled in the art. See, e.g., Niu et al., 2000. *Plant Cell Rep. V*19:304-310; Chang and Yang, 1996, *Bot. Bull. Acad. Sin., V*37:35-40 and Han et al., 1999, *Biotechnology in Agriculture and Forestry, V*44:291 (ed. by Y. P. S. Bajaj), Springer-Vernag.

Genetically Modified (Transgenic) Plants/Plant Species/Plant Cells/Plant Tissues Also disclosed herein are plants and plant cells genetically modified by introduction of the disclosed gene editing constructs and expression vectors to display increased salt and drought resistance.

In some embodiments, the genetically modified plant comprises a plant that is modified to express an exogenous nucleic acid encoding a crassulacean acid metabolism (CAM)-specific phosphoenolpyruvate carboxylase (PEPC).

In some embodiments, the exogenous nucleic acid encodes a PEPC gene of a CAM plant species. In a specific embodiment, the CAM plant species is selected from the group consisting of genera *Agave, Kalanchoe, Phalaenopsis, Ananas* and *Crassula*. In a specific embodiment, the CAM plant species is selected from the group consisting of *Kalanchoe fedtschenkoi, Agave Americana, Phalaenopsis equestris* and *Ananas comosus*.

In a specific embodiment, the CAM plant species is *Agave Americana*. In a specific embodiment, the CAM-specific PEPC comprises an amino acid sequence substantially identical with SEQ ID NO: 19, and a nucleic acid sequence substantially identical with SEQ ID NO: 18.

In some embodiments, the exogenous CAM-specific PEPC is expressed constitutively in the genetically modified plant. In some embodiments, the CAM-specific PEPC is expressed in the genetically-modified plant in a temporally controlled manner. In a specific embodiment, the temporally controlled manner comprises expression of the CAM-specific PEPC during the daytime. In a specific embodiment, the temporally controlled manner comprises expression of the CAM-specific PEPC during the night time.

In some embodiments, the exogenous nucleic acid encodes a PEPC is from a CAM plant species. In a specific embodiment, the CAM plant species is selected from the group consisting of *Agave americana, Kalanchoe fedtschenkoi, Phalaenopsis equestris, Ananas comosus* and *Crassula perforata*.

In some embodiments a plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

In some embodiments, the transgenic plants express the disclosed genes in a tissue-specific manner. In some embodiments, the genes are expressed from nucleic acid constructs that comprise a cell type or tissue type-preferential promoter. As used herein, a "cell type- or tissue-preferential promoter" refers to a promoter that drives expression preferentially in the target tissue, but may also lead to some expression in other cell types or tissues as well. In a specific embodiment, the disclosed genes are expressed in the leaf tissue.

Initial and immediate application of the disclosed methods can be made in the bioenergy crops *Populus* and switchgrass, but the application can be extended to other bioenergy crops such as corn, other sources of lignocellulosic biomass and other model plants e.g., *Salix, Miscanthus*, rice, wheat, soybean and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, miscanthus, oat, rice, rye, ryegrass, sorghum, sudangrass, sugarcane, sweet corn, switchgrass, turf grasses, timothy and wheat. Gymnosperms such as fir, pine and spruce can also be suitable.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

Example 1: CAM-Specific PEPC in *Agave americana*

Figure 1B:
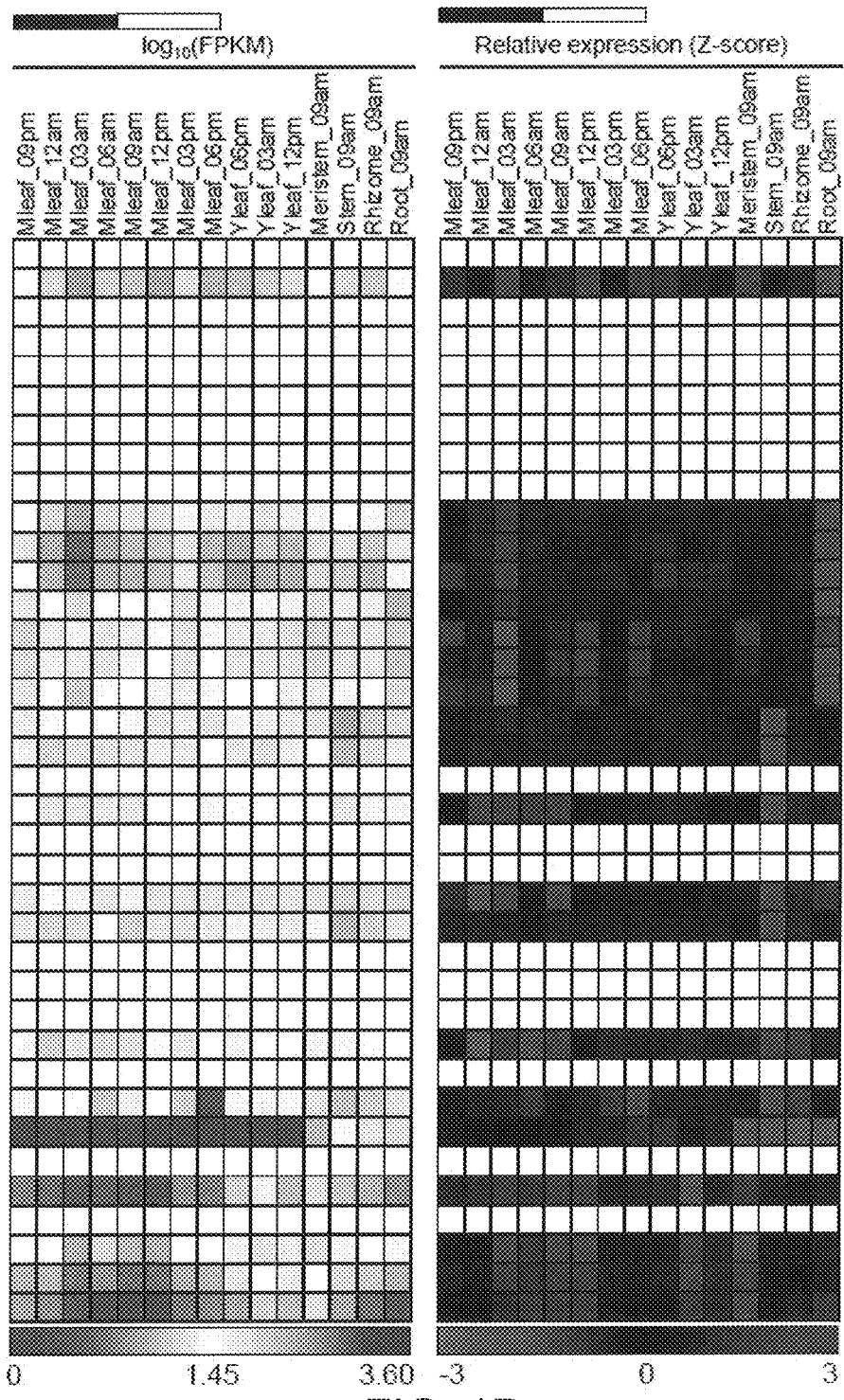

Through a tBLASTn search against *A. americana* transcriptomics data (Abraham P E. et al., 2016. *Nature Plants*, 2: 16178. 500) using the PEPC protein sequences of *Arabidopsis thaliana* as queries, the inventors identified a total of 21 transcripts encoding PEPC in *A. americana*. Several types of PEPC are present in plants, including plant-type PEPCs (PTPCs) and one bacterium-type PEPC (BTPC) (O'Leary B. et al. 2011. *Biochemical Journal*, 436: 15-34; Shi J. et al. 2015. *Plant Physiology*, 167: 671-681). The plant-type PEPCs studied so far are classified into four groups, including $C_3$, $C_4$ and CAM-types from photosynthetic tissues and root-type from non photosynthetic tissue (Masumoto C. et al. 2010. *PNAS*, 107: 5226-5231). In order to gain insight into the evolutionary relationships among PTPCs, the inventors constructed a phylogenetic tree using the 21 predicted *Agave* PEPC transcripts and the $C_3$-, $C_4$-, CAM- and root-type PEPCs from rice (*Oryza sativa*), maize (*Zea mays*), wheat (*Triticum aestivum*), sugarcane (*Saccharum* spp.), sorghum (*Sorghum bicolor*), foxtail millet (*Setaria italica*) and orchid (*Phalaenopsis equestris*) (Masumoto C. et al. 2010. *PNAS*, 107: 5226-5231; Yang X. et al. 2017, *Nature Communications* 8: 1899). Phylogenetic analysis of the plant-type PEPCs indicates that Aam080248 (named AaPEPC1) belongs to CAM-type PEPC (FIG. 1A). The results also showed the CAM- and $C_4$-type PEPCs belong to different clades, suggesting that these two PEPC types evolved independently. Using the quantitative gene expression data obtained from the RNA-Seq analysis of 15 tissues, including mature leaf (sampled at 8 time-points over a diel cycle), young leaf (3 time points), root, meristem, rhizome, and stem in *A. americana* (Abraham P E. et al., 2016. *Nature Plants*, 2: 16178. 500), the inventors obtained the expression pattern of the 21 PEPC transcripts (FIG. 1B), among which Aam080248 was the most abundant transcript in mature leaves, with a transcript abundance peak during the late afternoon just before the start of the dark period. These results consolidate the above computational prediction that the Aam080248 gene encodes the CAM-specific PEPC in *A. americana*.

Example 2: AaPEPC1 Binds to Phosphoenolpyruvate

Figures 2A, 2B, 2C:
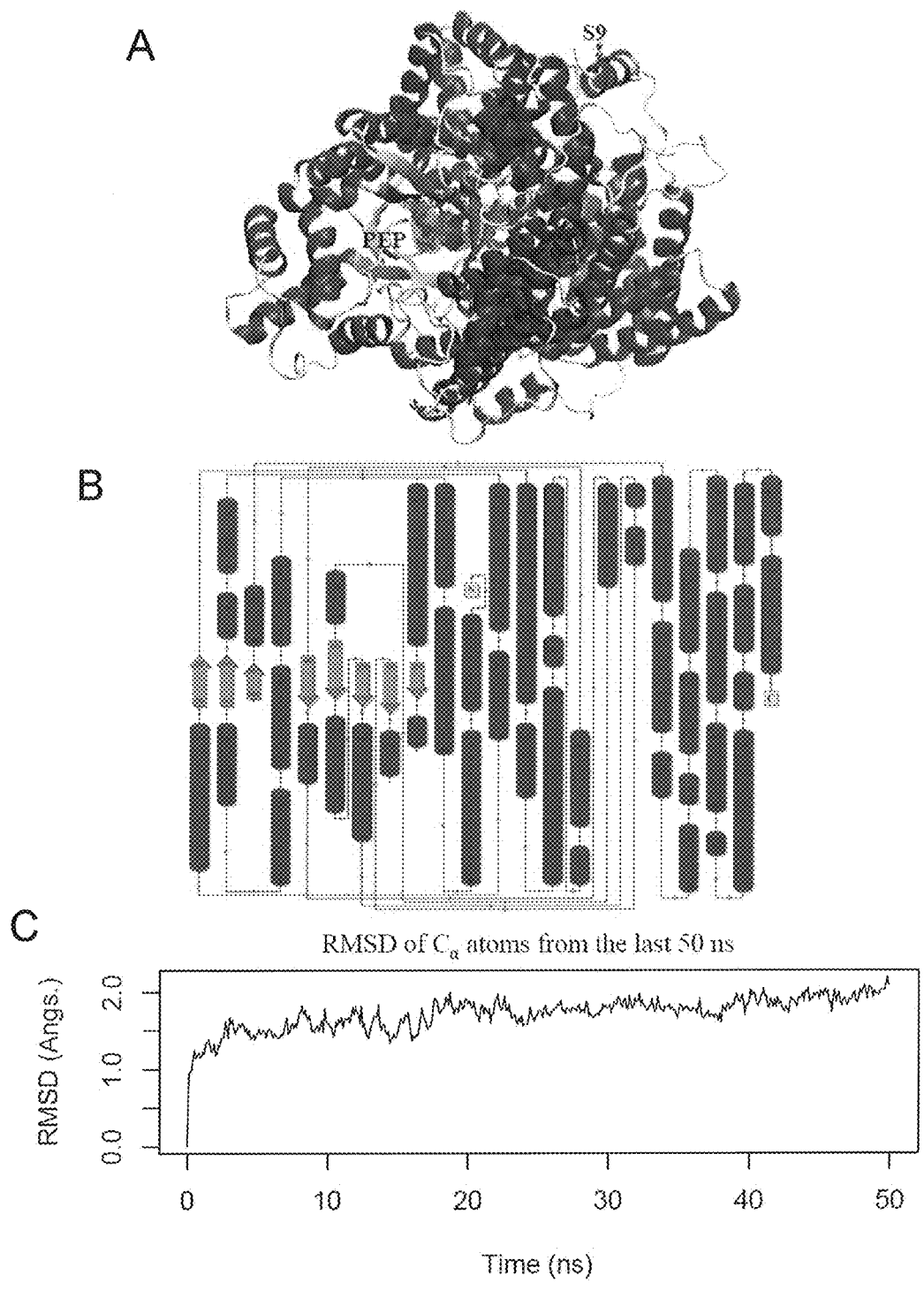
FIGS. 2A-2F. AaPEPC1 binds to phosphoenolpyruvate (PEP) substrate. (A) Left: AaPEPC1 structure selected from 200 ns molecular dynamics (MD) simulation that is closest to the average structure of the whole trajectory (RMSD=0.8 Å). The protein structure was shown in cartoons with helices in red, strands in yellow and coils/turns in white, respectively. A PEP substrate that binds to the β-barrel (yellow) active site is shown in sick and spheres. The plant-specific N-terminal serine residue (S9) is also shown. The binding position of the PEP substrate was obtained from the *Escherichia coli* PEPC-PEP complex (PDB entry 1JQN) (Matsumura H. et al., 2002. *Structure*, 10: 576 1721-1730). (B) A cartoon representation of the topology of AaPEPC1 structure. (C) The RMSD (Å) profile of the final 50 ns of the MD simulation. The deviations of all snapshots to the average MD structure are 1.4±0.2 Å (not shown). (D) Ramachandran plot of the *E. coli* (PDB entry 1JQN) PEPC. (E) *Zea mays* $C_4$-type PEPC (PDB entry 5VYJ). (F) and AaPEPC1 (the final snapshot of the 200 ns MD trajectory).
Figures 2D, 2E, 2F:
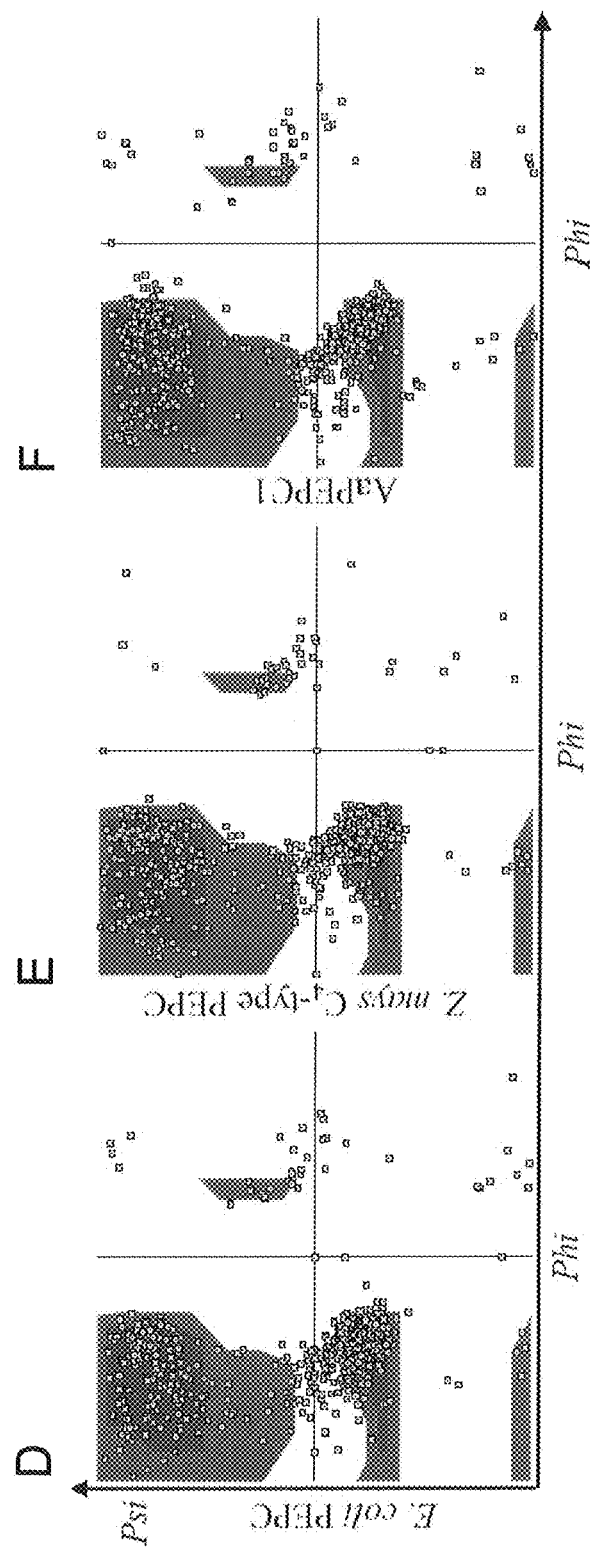

Phosphoenolpyruvate (PEP) is the substrate for PEPC enzymes (Kai Y. et al. 2003. *Arch Biochem Biophys*, 414:

170-179; Gonzalez-Segura L. et al. 2018. *Journal of Biological Chemistry:* jbc. RA118. 002884). To understand whether or not AaPEPC1 binds to PEP, the inventors developed protein structural model using I-TASSER (v.5.1) accompanied by 200 ns molecular dynamics (MD) simulation (FIGS. 2A-2C). The last 50 ns of the MD trajectory was taken to refine the AaPEPC1 structure. The root mean square deviation (RMSD) of the α-carbon atoms of all residues is ca. 2.0 Å (FIG. 2C), which is reasonable for fluctuations of the 964 amino acids (AA) protein. From the last 50 ns MD trajectory, the snapshot that is closest to the average structure (with RMSD=0.8 Å) was selected as the final model (FIGS. 2A-2B). Since the crystal structures of bacterial (*Escherichia coli*) PEPC (PDB entry 1JQN) and *Z. mays* $C_4$-type PEPC (PDB entry 5VYJ) are well characterized (Matsumura H. et al., 2002. *Structure*, 10: 576 1721-1730; Kai Y. et al. 2003. *Arch Biochem Biophys*, 414: 170-179; González-Segura L. et al. 2018. *Journal of Biological Chemistry: jbc. RA*118. 002884), in this study, the inventors compared the protein structure of AaPEPC1 with the *E. coli* PEPC and the *Z. mays* $C_4$-type PEPC. In line with *E. coli* PEPC and *Z. mays* $C_4$-type PEPC, the AaPEPC1 model is dominated by α-helix regions (546 AAs, 57.7%). The Ramachandran plot of the AaPEPC1 structure has 93.4% (804 AAs) in the most favorable regions, compared to 92.6% for the *E. coli* PEPC and 90.5% for the *Z. mays* $C_4$-type PEPC, respectively (FIG. 2D-2F). In addition, 5.2% (45 AAs) of AaPEPC1 are in the additional allowed regions (7.1% for *E. coli* PEPC and 8.7% for *Z. mays* $C_4$-type PEPC), 1.2% (10 AAs) are in the generously allowed regions (0.1% for *E. coli* PEPC and 0.2% for *Z. mays* $C_4$-type PEPC) and 0.2% (2 AAs) are in disallowed regions (0.1% for *E. coli* PEPC and 0.3% for *Z. mays* $C_4$-type PEPC). The N-terminus of AaPEPC1 contains the plant-specific serine residue (S9) (FIG. 2A), which is located in the middle of an α-helix flanked by a long loop region. This serine residue, however, was absent in bacterial PEPC (e.g., *E. coli* PEPC, PDB entry 1JQN) or, was not solved in the *Z. mays* $C_4$-type PEPC, potentially owing to the loop next to the α-helix (FIGS. 2A-2B). The AaPEPC1 model suggests that the AaPEPC1 can efficiently bind to PEP, which is bound by H171 and R640 where R640 is located at a GRGGXXGR640GG motif (FIG. 2A) and is overlapped with R647 in *Z. mays* $C_4$-type PEPC, whereas H171 is overlapped with H177 in *Z. mays* $C_4$-type PEPC, and hence both H171 and R640 in AaPEPC1 may directly participate in the carboxylation reaction as proposed in the $C_4$-type PEPC (Kai et al. 2003). In addition, based on the PEP-AaPEPC1 complex model, R449 (R456 in *Z. mays* $C_4$-type PEPC) may also be involved in PEP binding and the PEPC catalysis.

Example 3: Development of Transgenic Lines of Tobacco Overexpressing AaPEPC1

Figures 11A, 11B:
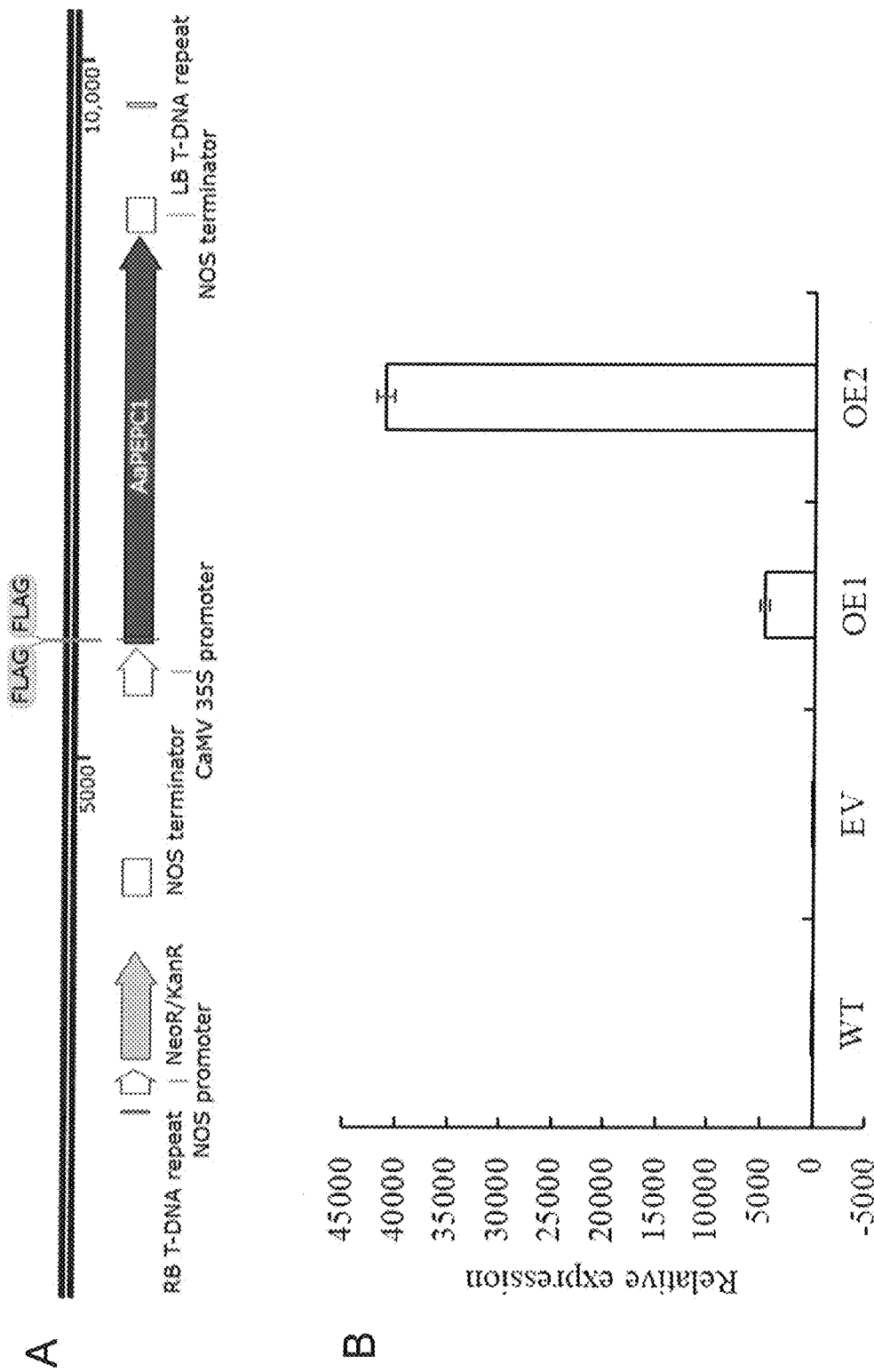
FIGS. 11A-11B. Development of transgenic lines of tobacco overexpressing *Agave americana* PHOSPHOENOLPYRUVATE CARBOXYLASE (AaPEPC1). (A) Schematic representation of the DNA construct developed for the overexpression of AaPEPC1 in transgenic tobacco. CaMV35S: cauliflower mosaic virus 35S; NOS: nopaline synthase; KanR: kanamycin resistance gene as a selection marker for screening transgenic plants; "LB" and "RB": the left and right borders of T-DNA, respectively. The image was generated with SnapGene software. (B) Quantitative reverse transcription PCR (qRT-PCR) analysis to detect the expression of AaPEPC1 in transgenic plants expressing AaPEPC (OE1, OE2), empty vector (EV), and wild-types (WT).

After the inventors identified the CAM-isoform of PEPC, the inventors tested the hypothesis that ectopic expression of the AaPEPC1 would bring the $C_3$ plant a step closer toward the CAM state and consequently enhance photosynthetic $CO_2$ fixation and abiotic stress tolerance in tobacco. The AaPEPC1 coding sequences were fused behind the cauliflower mosaic virus 35S (CaMV35S) promoter in a binary vector pBI121 to yield p35S::AaPEPC1 for transformation into tobacco (FIG. 11A). The p35S::AaPEPC1 vector and empty vector (pBI121, EV) were transferred into tobacco via *Agrobacterium tumefaciens*-mediated genetic transformation. Transformants harboring a single copy of inserted T-DNA were identified from the segregation ratio for kanamycin resistance. Two T2 transgenic homozygous lines (p35S::AaPEPC1_OE1 and p35S::AaPEPC1_OE2) exhibiting different expression level of the AaPEPC1 were randomly selected as representative lines for subsequent phenotype observation (FIG. 11B).

Figures 3A, 3B:
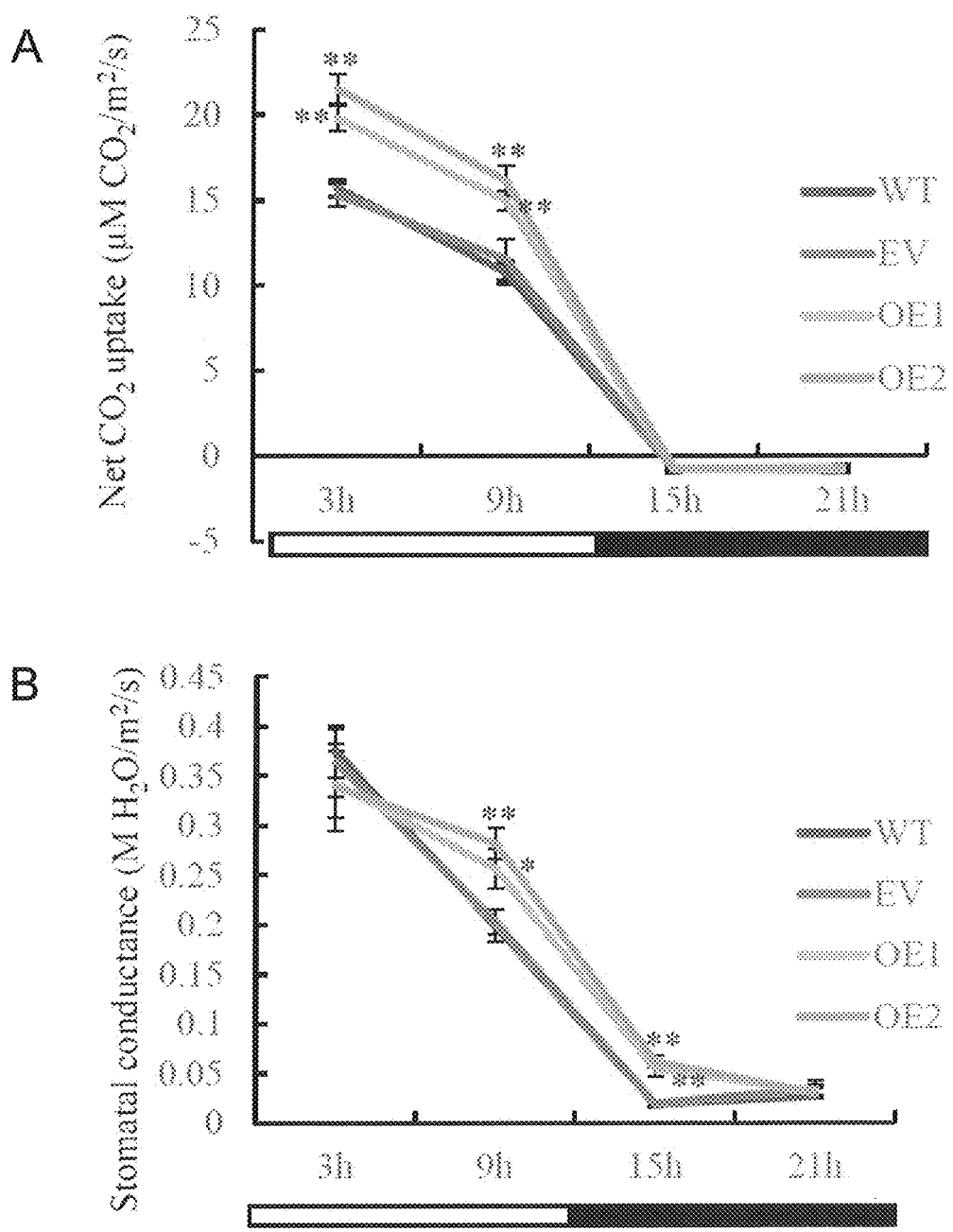
FIGS. 3A-3D. Photosynthetic performance of the AaPEPC1-overexpressing tobacco plants. (A) Photosynthetic rate, (B) stomatal conductance, (C) transpiration rate and (D) instantaneous water-use efficiency (WUE) of the transgenic plants expressing AaPEPC1 (OE1, OE2), empty vector control (EV) and wild-type plants (WT). White and black bars indicate daytime (12-hour) and nighttime (12-hour), respectively. X-axis represents the time after the beginning of the light period. Values represent means± SD. * and ** significant difference from that of WT at $P<0.05$ and $P<0.01$, respectively, by one-way ANOVA analysis with post-hoc Tukey HSD.
Figures 3C, 3D:
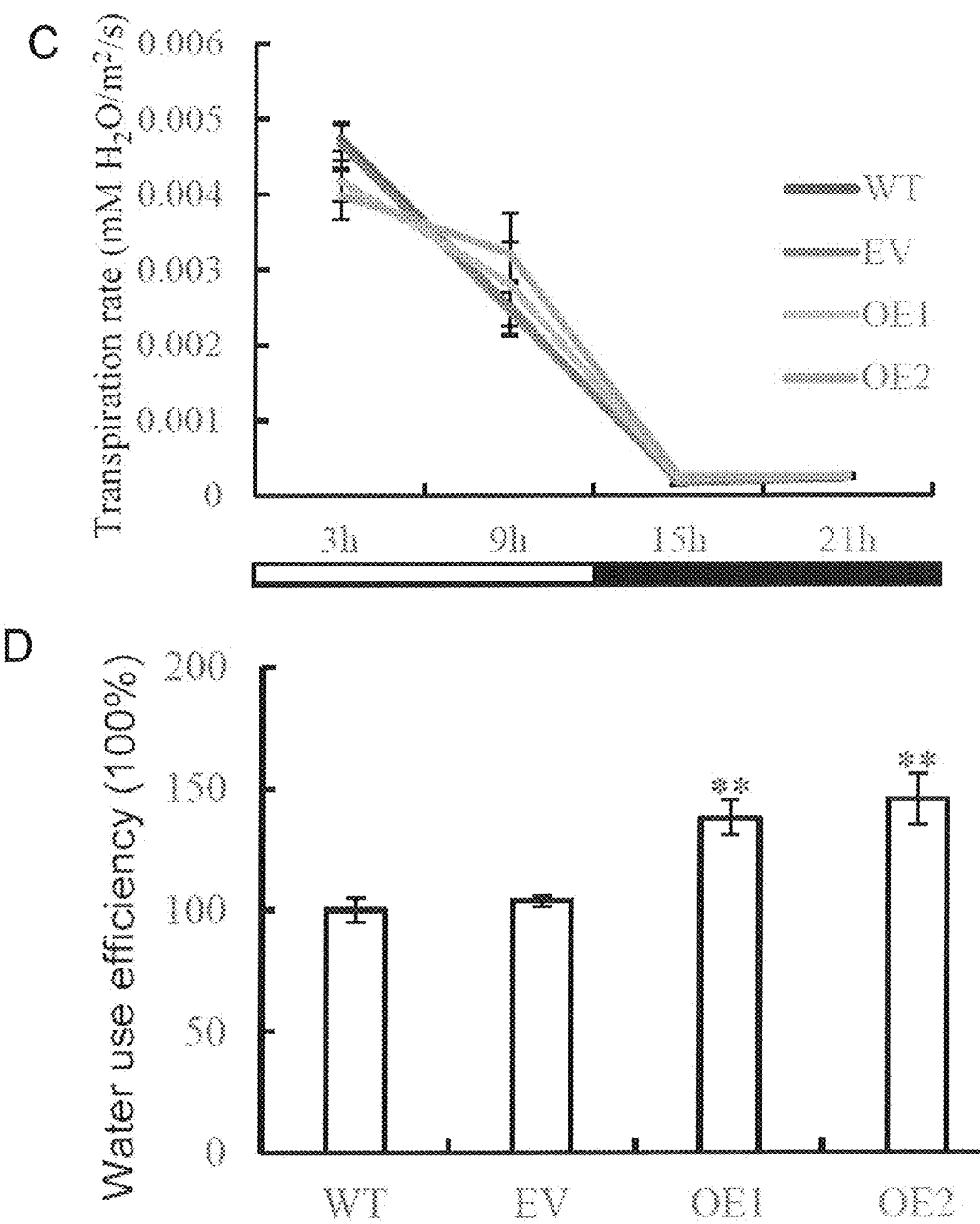
Figure 12:
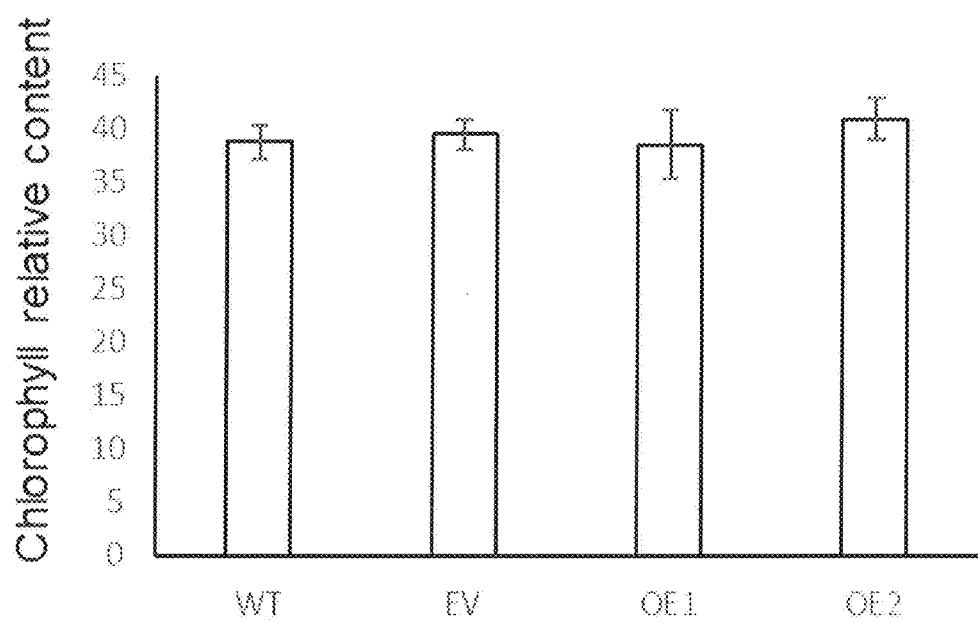
FIG. 12. Chlorophyll relative content in the leaves of transgenic plants (OE1, OE2) expressing *Agave americana* PHOSPHOENOLPYRUVATE CARBOXYLASE (AaPEPC1) or empty vector (EV), and wild-types (WT) grown in pots under normal growth conditions. Values represent means±SD.

Example 4: Overexpression of AaPEPC1 Increases Photosynthetic Rate and Water-Use Efficiency In order to assess whether the constitutive overexpression of AaPEPC1 affects photosynthetic performance, the inventors performed gas exchange analysis of the transgenic tobacco plants over expressing AaPEPC1, along with empty vector (EV) and wild-type (WT) control plants, grown under normal conditions (12 h light/12 h dark photoperiod; without drought- or salt-stress) at four time points (i.e., 3 h, 9 h, 15 h and 21 h after the beginning of the light period). The transgenic plants over-expressing AaPEPC1 showed significantly higher photosynthetic rates than WT and EV controls in the daytime (FIG. 3A). The stomatal conductance of the transgenic plants expressing AaPEPC1 were lower in the morning (at 3 h after the beginning of the light period), but significantly higher in the late afternoon (at 9 h after the beginning of the light period) and during the night period (at 15 h after the beginning of the light period) than that in controls (FIG. 3B). Transpiration rates of the transgenic plants were lower at 3 h and slightly higher at 9 h after the beginning of the light period than that in controls, and similar to controls during the night period (FIG. 3C). Water-use efficiency (WUE) of transgenic plants was significantly higher than that of the controls (FIG. 3D). In addition, relative chlorophyll content of the transgenic plants and WT were measured, and no significant difference was found among the transgenic plants and WT (FIG. 12).

Example 5: The Impact of AaPEPC1 Overexpression on the Accumulation of Malate and Glucose PEPC functions in the production of malate, which is a key intermediate of the tricarboxylic acid (TCA) cycle linking lipids and glucose metabolisms with photosynthesis in plants (Nunes-Nesi A. et al. 2011. *Plant Physiology*, 155: 101-107; Shi J. et al. 2015. *Plant Physiology*, 167: 671-681). The diel fluctuation in malate level represents a central biochemical requirement of the CAM photosynthesis pathway (Borland et al. 2014). Also, glycolysis and gluconeogenesis pathways (breakdown and synthesis of glucose) supply substrates (PEP and pyruvate) for nocturnal primary carboxylation and daytime decarboxylation reactions, respectively, and are thus essential for CAM plants (Borland A M. et al., 2014. *Trends in Plant Science*, 19: 327-338; Bräutigam A. et al. 2017. *Plant physiology*, 174: 473-477).

Figures 4A, 4B, 4C:
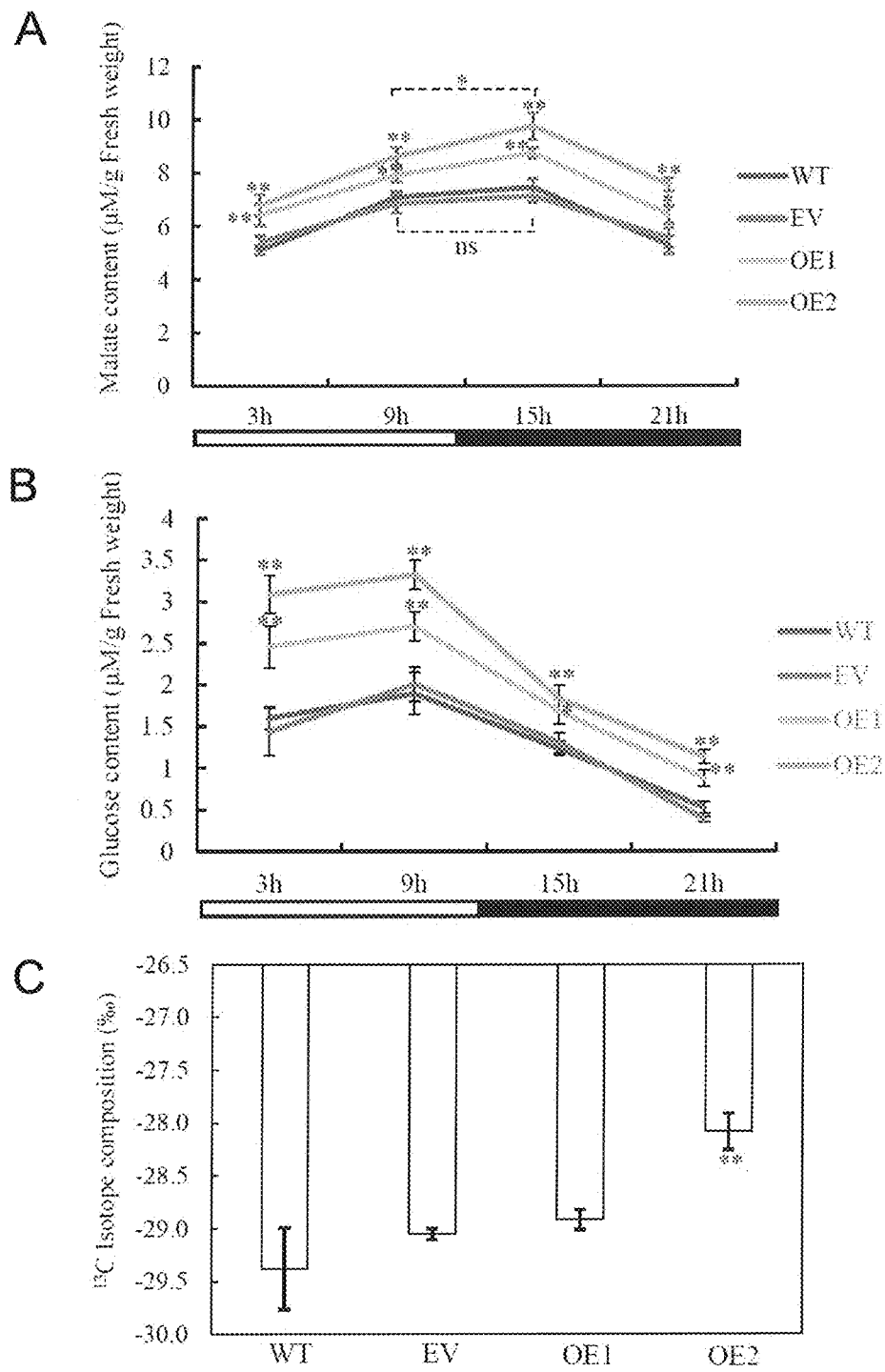
FIGS. 4A-4C. Malate content, glucose content and $^{13}C$ isotope composition of transgenic tobacco plants expressing AaPEPC1. (A) Malate content of the transgenic plants expressing AaPEPC1 (OE1, OE2), empty vector control (EV) and wild-type plants (WT). White and black bars indicate daytime (12-hour) and nighttime (12-hour), respectively. X-axis represents the time after the beginning of the light period. (B) Glucose content of the transgenic plants expressing AaPEPC1, EV and WT. (C) $^{13}$C isotope composition of the transgenic plants and WT. Values represent means±SD. * and ** significant difference from that of WT at $P<0.05$ and $P<0.01$, respectively, by one-way ANOVA analysis with post-hoc Tukey HSD. ns=non-significant.

To determine the impact of AaPEPC1 overexpression on malate and glucose production in transgenic tobacco, the malate and glucose contents were measured with standard enzyme-linked spectrophotometric methods at 4 time points (i.e., 3 h, 9 h, 15 h and 21 h after the beginning of the light period). The transgenic plants showed higher malate and glucose contents than WT and EV controls at all the four time points during day and night (FIGS. 4A-4B). Furthermore, the transgenic plants expressing AaPEPC1 showed a significant accumulation of malate content at 15 h compared with that at 9 h after the beginning of the light period, while no significant difference was found between the malate contents at 15 h and 9 h in controls plants (FIG. 4A). The rewired diel malate accumulation-depletion pattern suggests that AaPEPC1 overexpression affected primary carboxylation in transgenic plants. Also, the inventors found that higher amount of glucose was breakdown in the early night (at 15 h after the beginning of the light period) in the transgenic plants compared with control plants (FIG. 4B), suggesting that overexpression of the AaPEPC1 enhances the glycolysis pathway and consequently supplies more substrates for primary carboxylation.

Example 6: AaPEPC1 Overexpression Changes Stable Carbon Isotope Ratio

Stable carbon isotope ratio $\delta^{13}C$ ($^{13}C/^{12}C$) is a broadly accepted indicator of the extent to which the biomass is derived from PEPC-mediated $CO_2$ fixation in plants, because PEPC discriminates less against $^{13}C$ than Rubisco, the enzyme responsible for most net $CO_2$ uptake in $C_3$ photosynthesis plants during the light period. The positive correlation between the $\delta^{13}C$ values and CAM activity has been demonstrated to be a simple and reliable method for determining the type of photosynthesis, including $C_3$, $C_3$-CAM intermediate and CAM (Winter K. et al. 2002. *Plant Physiology*, 129: 1843-1851; Holtum J A. et al. 2004. *Trees* 18: 658-668; Zhang L. et al. 2016. *Plant Journal*, 86: 175-185). In this study, the inventors found the $\delta^{13}C$ values were significantly increased (i.e., became less negative) in the transgenic line (OE2), the expression level of AaPEPC1 in which is 7.74-fold higher than that in the other transgenic line (OE1), in comparison with the controls (FIG. 4C), indicating that this transgenic line was using PEPC for photosynthetic carbon assimilation and shifted toward CAM photosynthesis. In addition, $\delta^{13}C$ has been also demonstrated to be a simple and reliable measure of WUE, and the negative correlation between the two metrics has been used as an indirect method for the selection of crops with improved WUE (Chen J. et al. 2011. *Plant, Cell & Environment* 34: 2009-2023). Thus, the $\delta^{13}C$ results also support the finding that overexpression of AaPEPC1 enhanced the WUE of transgenic plants.

Example 7: CAM-Related Genes are Up-Regulated by AaPEPC1 Overexpression

Figure 5A:
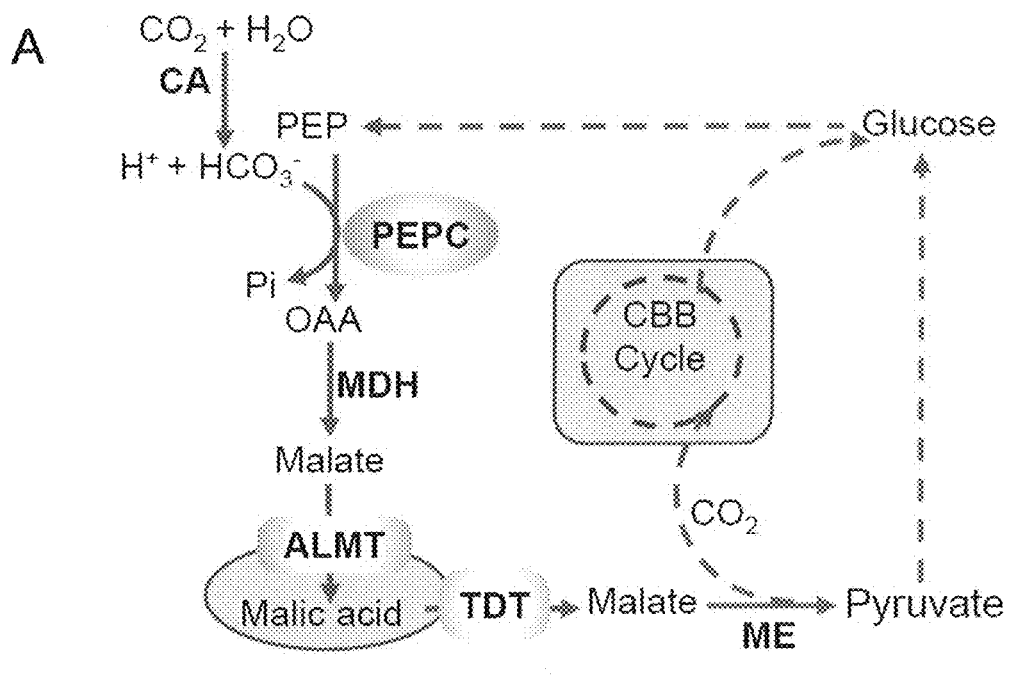
FIGS. 5A-5F. Relative expression level of the orthologs of CAM pathways genes in the AaPEPC1-overexpressing tobacco plants. (A) Diagram of the CAM pathway depending on malic enzyme (ME) subtype (Yang et al. 2017, *Nature Communications* 8: 1899). CA: carbonic anhydrase; PEPC: phosphoenolpyruvate carboxylase; OAA: oxaloacetate; MDH: malate dehydrogenase; ALMT: aluminum-activated malate transporter; TDT: tonoplast dicarboxylate transporter; CBB: Calvin-Benson-Bassham. (B)-(F) Relative expression level of *Nicotiana sylvestris* carbonic anhydrase (NsyCA, XM_009805732.1), NsyMDH (XM_009784202.1), NsyALMT (XM_009797046.1), NsyTDT, (XM_009797970.1) and NsyME (XM_009781546.1), respectively. White and black bars indicate daytime (12-hour) and nighttime (12-hour), respectively. X-axis represents the time after the beginning of the light period. Values represent means±SD.
Figure 5B:
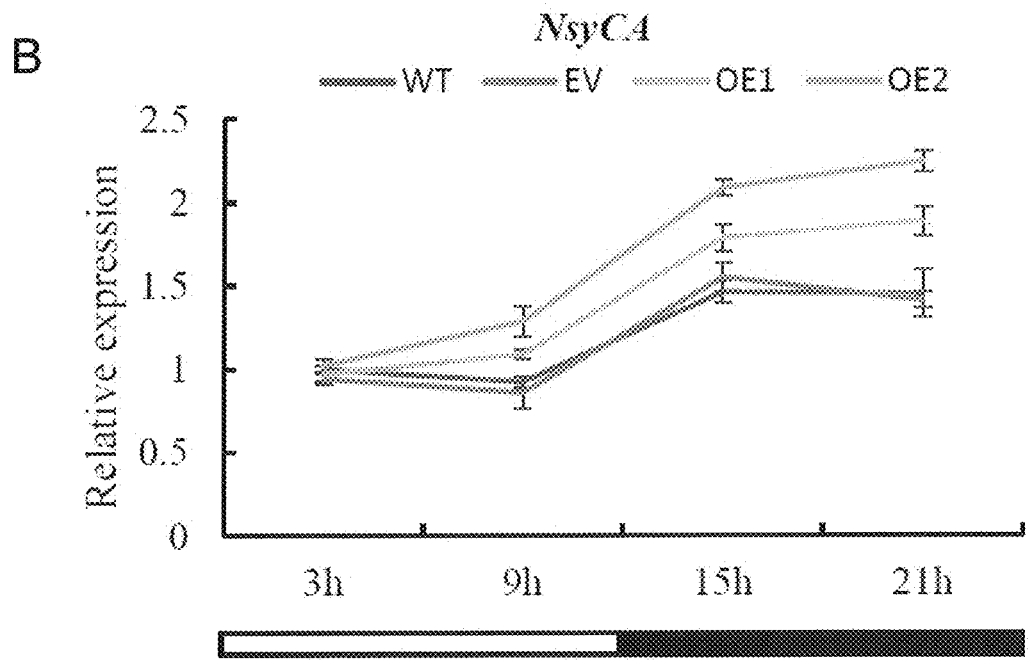
Figure 5C:
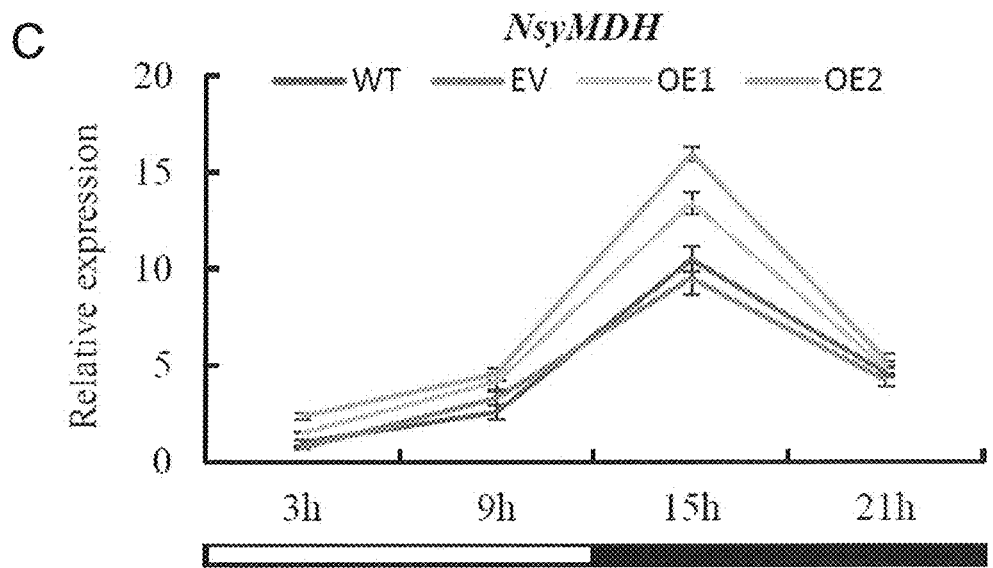
Figure 5D:
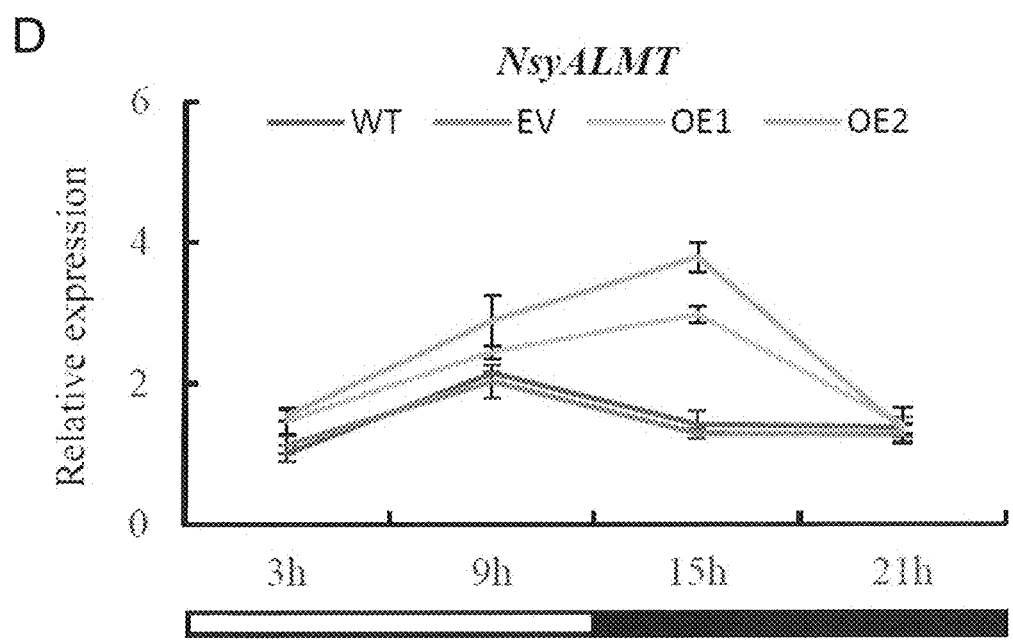
Figures 5E, 5F:
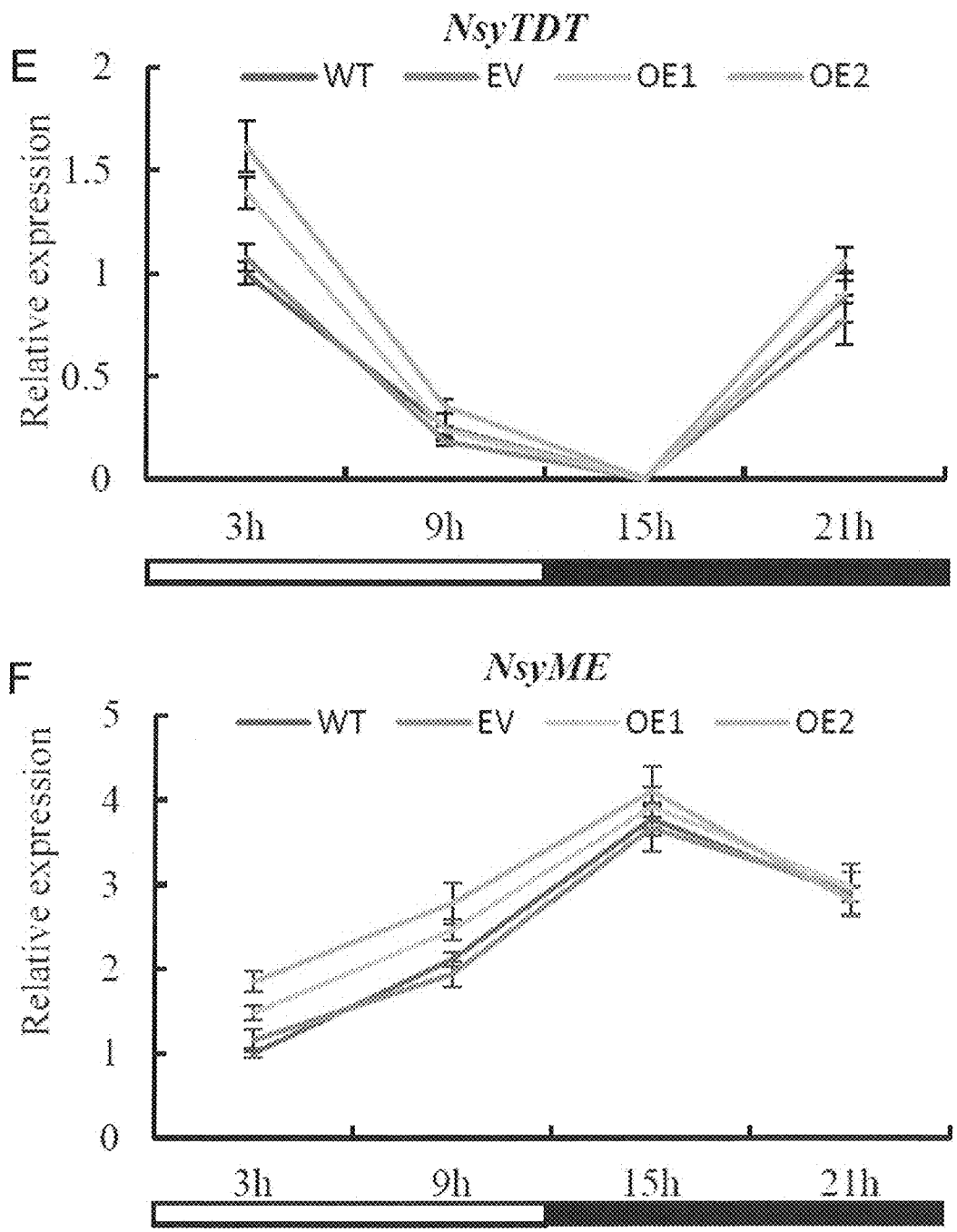

To test whether the re-programed changes in diel malate content will lead to feedback regulation of CAM pathway genes, expression of the orthologs of CAM genes in the transgenic and WT plants was analyzed using quantitative reverse transcription PCR (qRT-PCR) (FIG. 5A). The expression of carbonic anhydrase (NsyCA), an ortholog of CA which is responsive for rapid inter-conversion of carbon dioxide and water into carbonic acid, protons and bicarbonate ions in CAM, was increased in transgenic plants expressing AaPEPC1 compared with that in the controls at 9 h, 15 h and 21 h after the beginning of the light period (FIG. 5B). The expression levels of malate dehydrogenase (NsyMDH) (an ortholog of MDH which is responsive for catalyzing the oxidation of malate to OAA in CAM) and tonoplast aluminum-activated malate transporter (NsyALMT) (an ortholog of ALMT which is responsive for transporting malate into vacuole in CAM) in the transgenic plants were significantly higher than those in the controls at early night period (15 h after the beginning of the light period), while no significantly difference was found at other three time points (FIG. 5C-5D). The expression of tonoplast dicarboxylate transporter (NsyTDT) (an ortholog of TDT which is responsive for transporting malate out of vacuole in CAM) was significantly up-regulated in transgenic plants at early morning period (3 h after the beginning of the light period), while no significantly difference was found at other 3 time points (FIG. 5E). The expression level of malic enzyme (NsyME) (an ortholog of ME which is responsive for decarboxylation of malate in CAM) in transgenic AaPEPC1 plants was significantly increased during the day time and was similar with controls during the night time (FIG. 5F). These results demonstrate that overexpression of the AaPEPC1 up-regulated the expression of the orthologs of CAM pathway genes in transgenic plants.

Example 8: Impact of AaPEPC1 Overexpression on Biomass Production

Figure 6A:
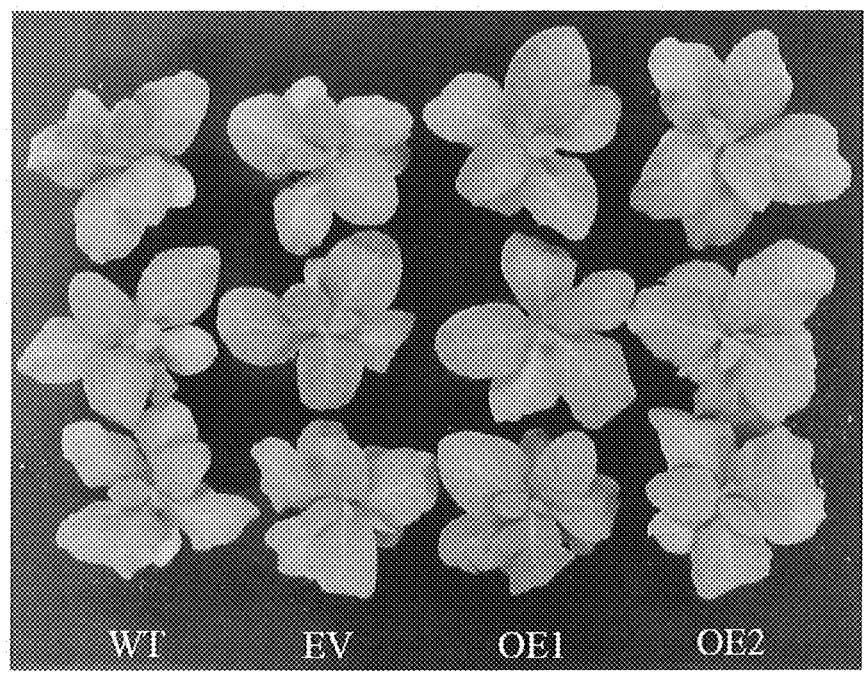
FIGS. 6A-6B. Growth characteristics of transgenic tobacco plants expressing AaPEPC1. (A) Phenotypes of transgenic plants (OE1, OE2) expressing AaPEPC1 or empty vector (EV), and wild-types (WT) grown in pots under normal growth conditions. (B) Dry weight (shoot and root) of transgenic plants and WT. Values represent means±SD. * and ** significant difference from that of WT at $P<0.05$ and $P<0.01$, respectively, by one-way ANOVA analysis with post-hoc Tukey HSD.
Figure 6B:
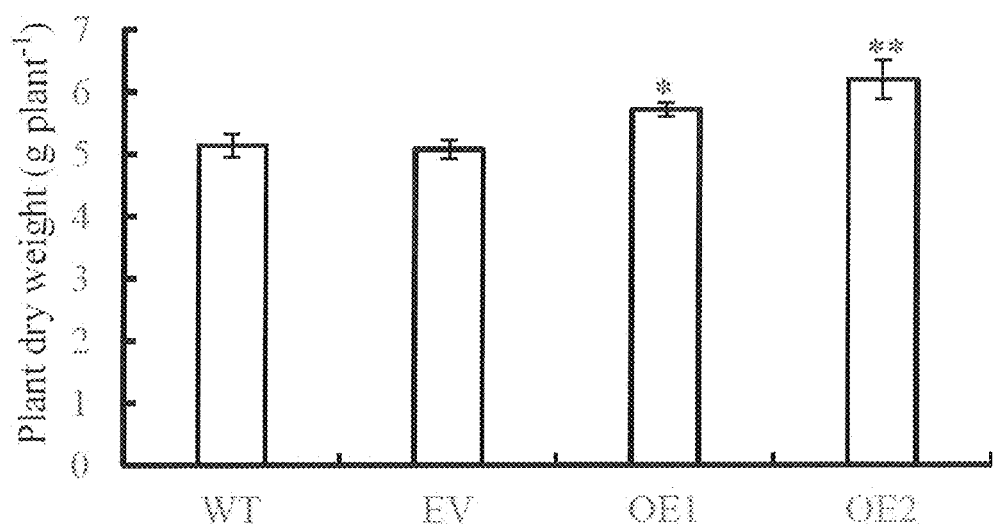

Based on the above, the inventors speculated that the higher photosynthetic rates, glucose content and $^{13}C/^{12}C$ isotope ratios measured in transgenic plants may result in improved biomass production. To test this speculation, the inventors examined the growth of the transgenic plants, along with EV and WT control plants, in growth chambers under well-water conditions. After 6-weeks of growth, the transgenic AaPEPC1 plants exhibited larger physical size than WT and EV controls (FIG. 6A). Dry weight of the transgenic AaPEPC1 plants was significantly increased in comparison with the control plants (FIG. 6B). This result indicates that AaPEPC1 overexpression increases biomass production in transgenic plants under normal conditions.

Example 9: Impact of AaPEPC1 Overexpression on Salt and Drought Tolerance

Figures 7A, 7B:
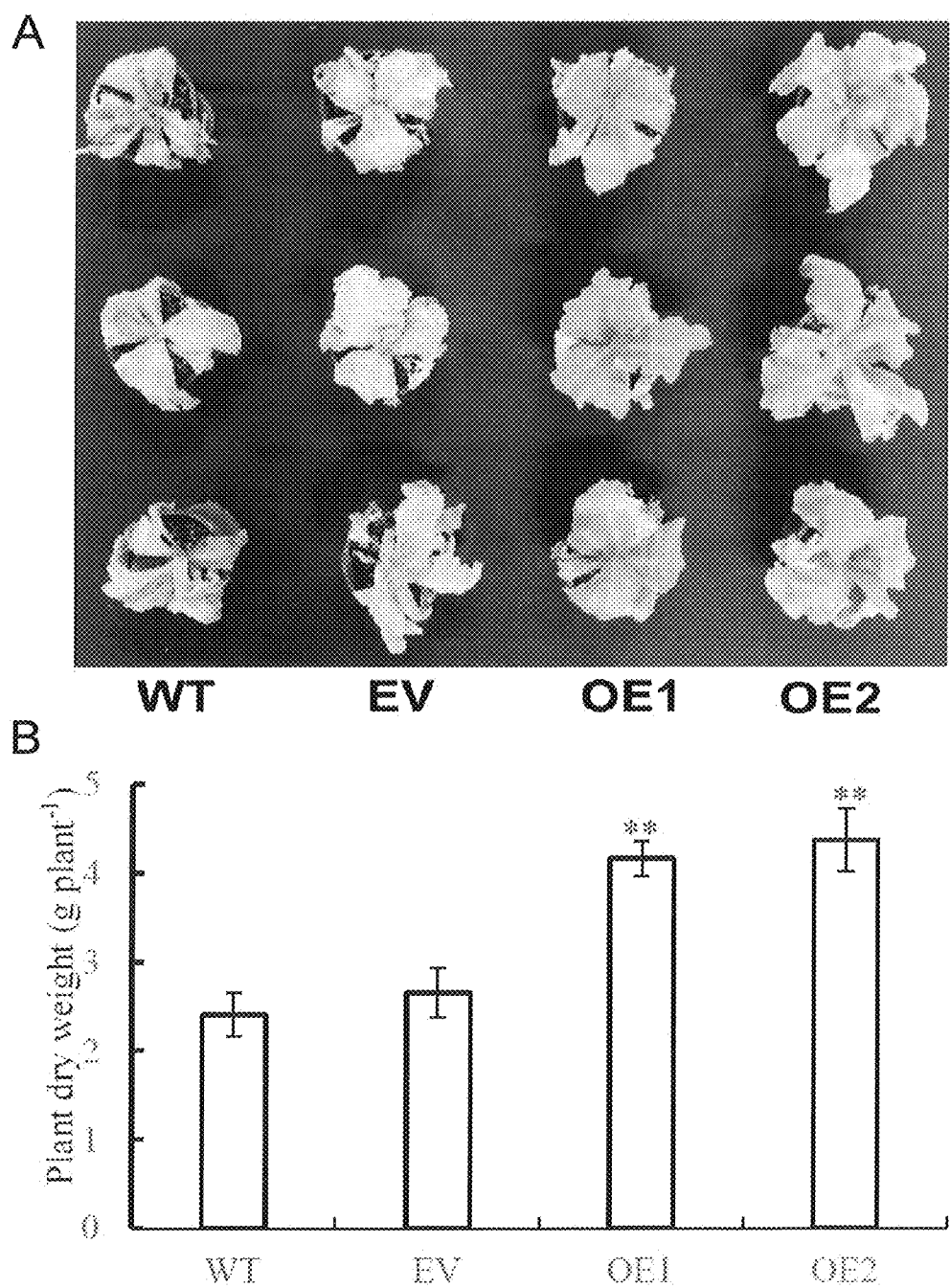
FIGS. 7A-7B. Responses of the AaPEPC1-overexpressing tobacco plants under salt stress. (A) Phenotypes of transgenic plants (OE1, OE2) expressing AaPEPC1 or empty vector (EV), and wild-types (WT) grown in pots under 200 mM NaCl stress. The plants were irrigated with 200 mM NaCl solution once every 2 days for 4 weeks. (B) Dry weight of transgenic plants and WT. Values represent means±SD. * and ** significant difference from that of WT at $P<0.05$ and $P<0.01$, respectively, by one-way ANOVA analysis with post-hoc Tukey HSD.

Most crop plants are susceptible to salinity, with their growth inhibited or even completely prevented by NaCl concentrations of 100-200 mM, resulting in plant death (Munns R et al. 1986. *Functional Plant Biology*, 13: 143-160; Acosta-Motos J R. et al., 2017. *Agronomy*, 7: 18). To investigate whether overexpression of AaPEPC1 enhances. salt tolerance in transgenic plants, the transgenic AaPEPC1 plants, and EV and WT controls were grown in pots and irrigated with a 200 mL of 200 mM NaCl solution once every 2 days for 4 weeks. The salt-stress treatment caused the death of WT and EV control plants, while the transgenic plants overexpressing AaPEPC1 maintained growth (FIG. 7A). Dry weight of the transgenic plants were significantly increased compared to controls (FIG. 7B). These results demonstrate that overexpression of AaPEPC1 significantly enhances tolerance to salt stress in transgenic tobacco plants.

Figure 8A:
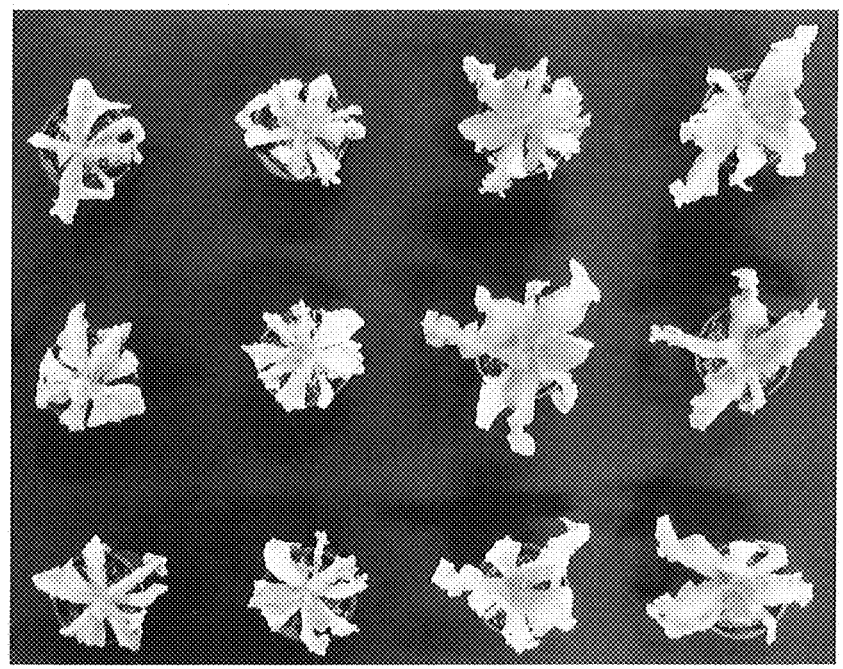
FIGS. 8A-8B. Responses of the AaPEPC1-overexpressing tobacco plants under drought stress. (A) Phenotypes of transgenic plants expressing PEPC (OE1, OE2) or empty vector (EV), and wild types (WT) grown in pots under drought stress. Transgenic plants and WT were grown in soil for 15 days without watering. (B) Dry weight of transgenic plants and WT. Values represent means±SD. * and ** significant difference from that of WT at $P<0.05$ and $P<0.01$, respectively, by one way ANOVA analysis with post-hoc Tukey HSD.
Figure 8A:
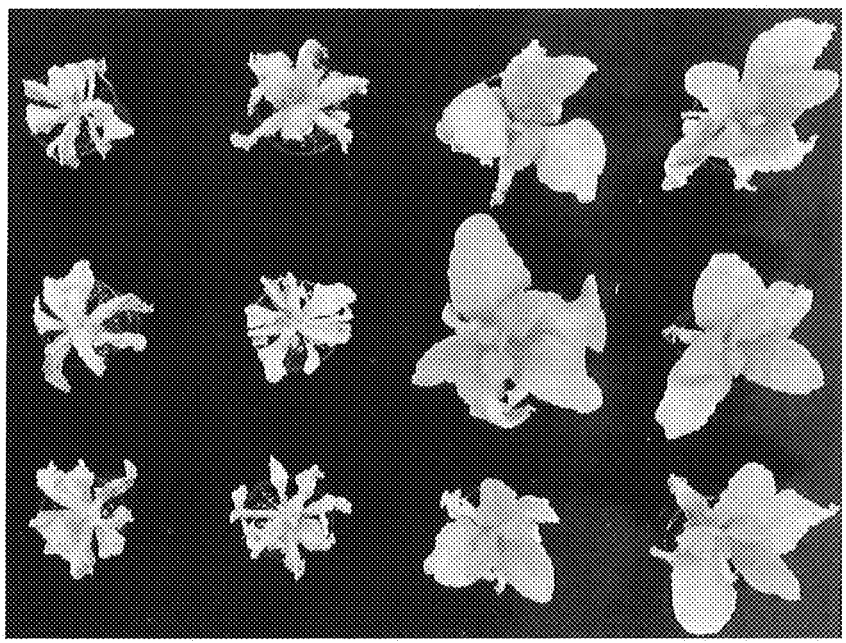
Figure 8B:
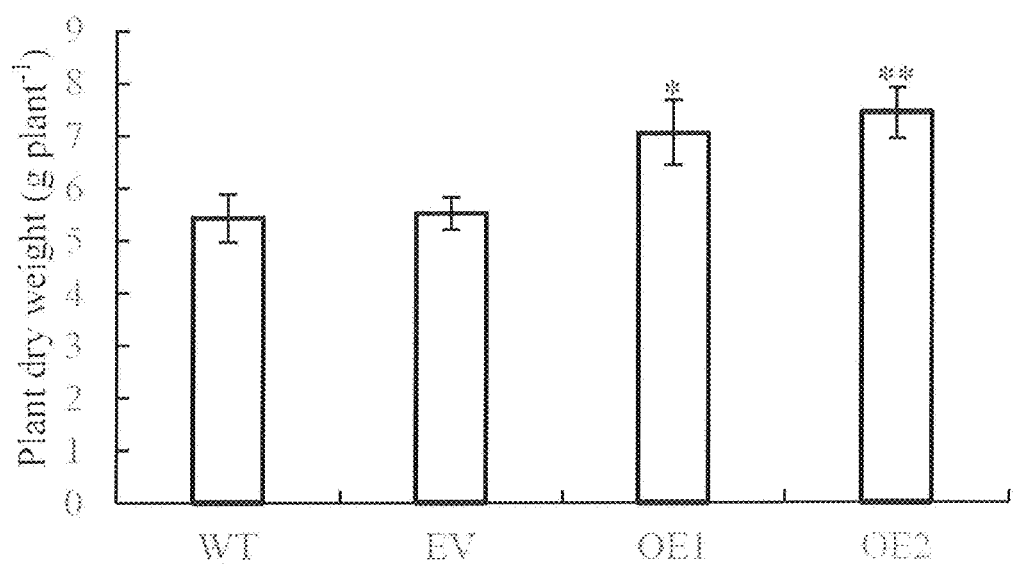

Based on a significant improvement in WUE in the transgenic plants expressing AaPEPC1 (FIG. 3D), the inventors hypothesized that AaPEPC1 overexpression could have beneficial impact on drought tolerance. To test this hypothesis, the transgenic AaPEPC1 plants, and EV and WT controls, were subjected to drought stress in growth chamber condition. After 15 days without watering, all WT and EV control plants displayed severe wilting (all leaves were severely curled and most of leaves had turned yellow/or were dead), whereas the growth of transgenic tobacco plants expressing AaPEPC1 was less affected and most upper leaves of transgenic plants were still green and expanded (FIG. 8A). After 3 days of rewatering, all WT and EV controls were nearly dead, whereas all transgenic lines survived and started to regrow (FIG. 8A). Dry weight of the transgenic plants was also significantly increased compared to the WT and EV controls (FIG. 8B). These results provide evidence that overexpression of AaPEPC1 improves the drought tolerance in the transgenic tobacco plants.

Example 10: Proline Biosynthesis is Enhanced by AaPEPC1 Overexpression

Figures 9A, 9B, 9C:
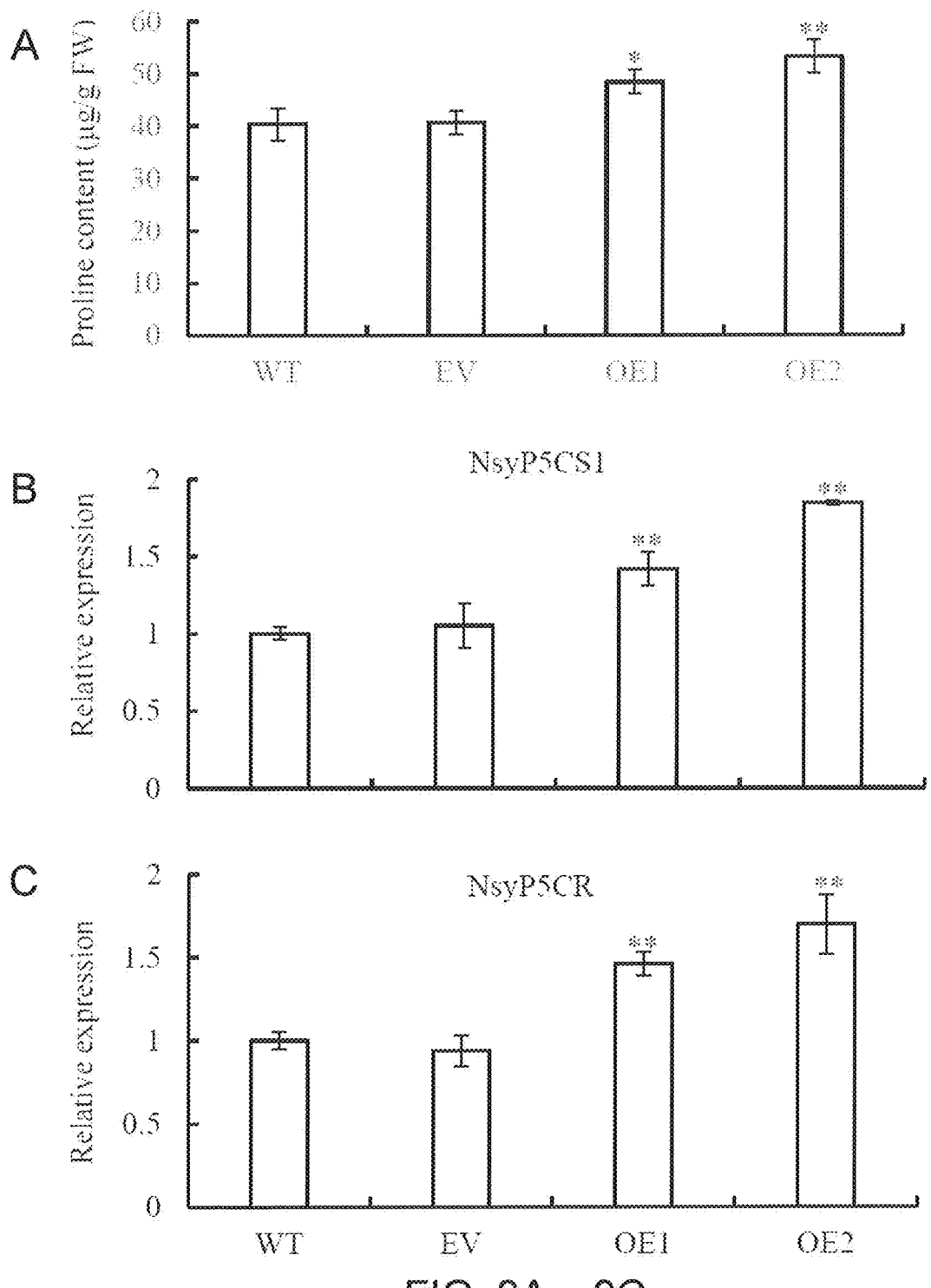
FIGS. 9A-9C. Changes of proline biosynthesis of AaPEPC1-overexpressing tobacco plants. (A) Proline content in the leaves of transgenic plants expressing PEPC (OE1, OE2) and empty vector (EV), and wild-types (WT). (B) and (C) Relative expression level of the proline biosynthesis gene pyrroline-5-carboxylate synthase (P5CS) and pyrroline-5-carboxylate reductase (P5CR) in the AaPEPC1-overexpressing tobacco plants. Values represent means±SD. * and ** significant difference from that of WT at $P<0.05$ and $P<0.01$, respectively, by one-way ANOVA analysis with post-hoc Tukey HSD.

PEPC plays a crucial role in nitrogen metabolism in *Arabidopsis* (Shi J. et al. 2015. *Plant Physiology*, 167: 671-681). Loss-of function of both PEPC1 and PEPC2 decreased the levels of glutamate in *Arabidopsis*. Glutamate can be converted into proline by two successive reductions catalyzed by pyrroline-5-carboxylate synthase (P5CS) and pyrroline-5-carboxylate reductase (P5CR) (Liu D. et al. 2014. *Plant Cell, Tissue and Organ Culture*, 117: 1-16). Proline plays important roles in stress tolerance, e.g., drought and salt stress tolerance, by regulating osmotic balance, activating ROS scavenging system, protecting membrane integrity and photosynthesis (Liu D. et al. 2014. *Plant Cell, Tissue and Organ Culture*, 117: 1-16). The inventors hypothesized that overexpression of AaPEPC1 could enhance the proline biosynthesis, and consequently increases the drought and salt stress tolerance in the transgenic plants. To test this hypothesis, proline content was analyzed in the transgenic AaPEPC1 plants, along with WT and EV controls. Proline contents in the transgenic plants expressing AaPEPC1 were significantly higher than that in the WT and EV controls (FIG. 9A). Furthermore, the expression levels of two key proline biosynthesis genes NsyP5CS and NsyP5CR were significantly higher in the transgenic AaPEPC1 plants in comparison with the WT and EV controls (FIGS. 9B-9C). These results support the hypothesis that overexpression of AaPEPC1 increases the drought and salt stress tolerance through the enhancement of proline biosynthesis.

Example 11

Figure 10:
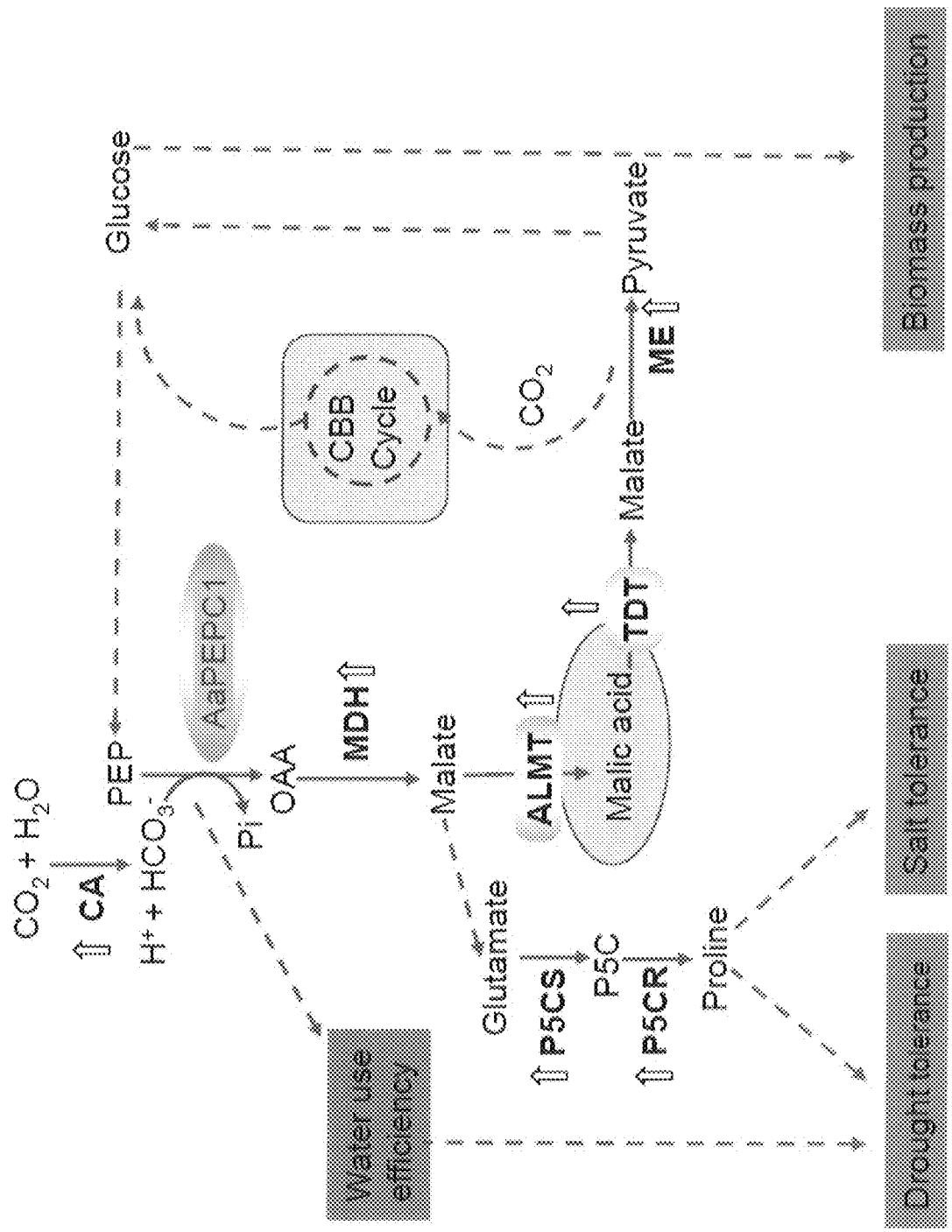
FIG. 10. Diagram showing the regulation of photosynthetic $CO_2$-fixation and abiotic stress tolerance in the 'turbocharging' plants with the AaPEPC1. Overexpression of the AaPEPC1, a highly abundant enzyme catalyzing the primary fixation of $CO_2$ in CAM plants, increases photosynthetic $CO_2$-fixation and water-use efficiency, and rewires the diel accumulation depletion pattern of malate and glucose. The re-programed malate-dependent carboxylation leads to feedback up-regulation of the orthologs of key step CAM pathway genes, i.e., nocturnal carboxylation and diurnal decarboxylation modules. The increased malate content up-regulates pyrroline-5-carboxylate synthase (P5CS) and pyrroline-5-carboxylate reductase (P5CR), which results in higher proline accumulation. Proline accumulation enhances salt and drought tolerance of the transgenic plants. Also, higher glucose content generated from the photosynthetic source will be transported as sucrose or glucose to the sink tissues and organs to promote cell proliferation, elongation, expansion, and to maintain energy and metabolic homeostasis, resulting in improved biomass production (Xiong Y. et al. 2013. *Nature*, 496: 181-186; Sheen J. 2014. *Journal of Plant Biology* 57: 67-79). Up arrow indicates up regulation of expression of genes coding these enzymes or content. CA: carbonic anhydrase; OAA: oxaloacetate; MDH: malate dehydrogenase; ALMT: aluminum-activated malate transporter; TDT: tonoplast dicarboxylate transporter; ME: malic enzyme; PEP: phosphoenolpyruvate; CBB: Calvin-Benson-Bassham.

Engineering of the water-conserving $CO_2$-concentrating mechanism of CAM has the potential to improve photosynthetic $CO_2$ fixation and abiotic stress tolerance in $C_3$ plants (Borland A M. et al., 2014. *Trends in Plant Science*, 19: 327-338; Yang X. et al. 2015. *New Phytologist*, 207: 491-504; Liu D. et al. 2018. *Plant Science*, 274: 394-401). This study achieved the first success in switching of $C_3$ toward CAM photosynthesis by engineering of one single gene from CAM plants. In this study, the inventors identified a CAM-type PEPC (AaPEPC1) in *A. americana* and transformed the AaPEPC1 gene into $C_3$ plant tobacco. Compared with WT and EV controls, the transgenic plants expressing AaPEPC1 expressed several CAM-like traits: 1) higher WUE, 2) higher stomatal conductance and malate accumulation at the onset of the dark period, 3) higher leaf carbon isotope ratio $\delta^{13}C$ values, and 4) upregulated expression levels of the orthologs of several key CAM pathway genes (FIGS. 3-5). This $C_3$-toward-CAM progression driven by AaPEPC1 improves photosynthetic $CO_2$-fixation, biomass production and tolerance to drought and salt stresses (FIG. 10). The overexpression of a single CAM-related gene can cause measurable changes in the transgenic plants physiology and performance was not expected based on the current understanding of CAM [and/or $C_4$] photosynthesis. This initial success provides a solid foundation for future effort to achieve a complete switch from $C_3$ to CAM photosynthesis through engineering additional CAM-related genes involved in carboxylation, decarboxylation stomatal movement, glycolytic-gluconeogenic pathway and carbohydrate turnover modules (Borland A M. et al., 2014. *Trends in Plant Science*, 19: 327-338; Yang X. et al. 2015. *New Phytologist*, 207: 491-504; Liu D. et al. 2018. *Plant Science*, 274: 394-401).

It is very interesting that AaPEPC1 overexpression increased the transcript abundance of several other CAM-related genes, including CA, MDH, ALMT, TDT and ME (FIG. 5). As a $CO_2$-fixation enzyme, AaPEPC1 is not able to directly regulate the expression of other genes at the transcription level. The inventors hypothesize that the change in cellular metabolic status caused the AaPEPC1 overexpression might rewire the regulatory network, resulting in upregulation of other CAM-related genes. This hypothesis can be tested through transcriptomic and metabolomic analysis of gain-of-function and loss-of-function AaPEPC1 mutants in the future. It was recently reported that PEPC activity is essential for core circadian clock operation in the obligate CAM species *Kalanchoë fedtschenkoi* (Boxall S F. et al. 2017. *Plant Cell*, 29: 2519-2536). Therefore, it would be interesting to investigate the impact of AaPEPC1 overexpression on the circadian rhythm in the transgenic plants in the future. In addition, on the premise of coordinated regulation of multiple CAM-related genes by over-expressing one key gene AaPEPC1, the inventors can argue that there is no need to transfer all the CAM pathway genes into $C_3$ species and consequently the inventors just need to focus on the engineering of a small number of "master" genes like AaPEPC1, which can upregulate the expression of multiple other CAM-related genes.

Although PEPC is well-known as a key enzyme for $CO_2$ fixation, its role in conferring resistance to salt stress in plants has not been very clear yet. In this study, the inventors clearly demonstrated that overexpression of AaPEPC1 significantly increased the salt tolerance in transgenic tobacco plants (FIG. 7), as a result of enhanced biosynthesis of proline (FIG. 9), which plays important roles in regulating osmotic balance, activating ROS scavenging system, protecting membrane integrity and photosynthesis (Liu D. et al. 2014. *Plant Cell, Tissue and Organ Culture*, 117: 1-16). $C_4$-type PEPC or $C_3$-type PEPC has been reported to be involved in drought tolerance (Qian B. et al. 2015. *Journal of Plant Physiology*, 175: 9-20; Liu X. et al., 2017. *Physiologia Plantarum*, 159: 178-200; Zhang C. et al. 2017. *Plant Physiology and Biochemistry*, 115: 328-342). However, the role of CAM-type PEPC in drought tolerance remained unclear. In this study, the inventors found that overexpression of the AaPEPC1 significantly increased the drought tolerance in the transgenic tobacco plants (FIG. 8). Also, the inventors found the transgenic AaPEPC1 plants exhibited higher WUE and $\delta^{13}C$ compared with controls (FIGS. 3D and 4C). The results of this disclosure indicate that the improvement of photosynthetic carbon metabolism in the transgenic AaPEPC1 plants enhances WUE and proline metabolism pathway, which results in improved drought tolerance (FIG. 10).

Recently, the photosynthesis and plant growth were significantly improved in tobacco plants through introducing a faster Rubisco of cyanobacterial origin (Lin M T. et al. 2014. *Nature*, 513: 547), accelerating recovery from photoprotection (Kromdijk J. et al. 2016. *Science*, 549 354: 857-861), or engineering synthetic glycolate metabolism pathways (South P F. et al. 2019. *Science*, 363: eaat9077). However, none of these approaches can enhance tolerance to drought or salt stresses. On the other hand, previous genetic engineering efforts made good progress in creating genetically-modified plants with enhanced tolerance to either drought stress (Singha D L. et al. 2017. *Plant Cell, Tissue and Organ Culture* 130: 577-589; Wang L. et al. 2018. *Plant Cell, Tissue and Organ Culture*, 133: 27-38) or salt stress (Roy S J. et al. 2014. *Current Opinion in Biotechnology* 26: 115-124; Liu D. et al. 2015. *Plant Cell, Tissue and Organ Culture*, 120: 701-715; Li R. et al. 2017. *Plant Science*, 262: 39-51), with very limited success in conferring tolerance to both drought stress and salt stress in a single transgenic line. In this study, the inventors created genetically-modified tobacco plants that have enhanced performance in multiple aspects: photosynthesis, plant growth, water use efficiency, drought tolerance, and salt tolerance. These pleiotropic effects of AaPEPC1-overexpression open a new door to genetic improvement of crops for sustainable bioenergy and food production on marginal lands to alleviate the challenge caused by human population growth, urbanization, and global climate change.

In conclusion, the inventors report the first successful effort of engineering of a CAM pathway gene to improve photosynthetic $CO_2$ fixation and abiotic stress tolerance in the model $C_3$ plant species tobacco. These findings have important implications for ultimate aspirations to engineer CAM into non CAM crops as a means of improving productivity, WUE and abiotic stress tolerance.

Example 12: Materials and Methods

Genome-Wide Analysis of the PEPC Gene Family

*Arabidopsis thaliana* PEPC sequences (AT1G68750.1, AT1G53310.1, AT3G14940.1 and AT2G42600.2) were retrieved and used as queries in BLAST searches against the *Agave americana* transcriptomics data (Abraham P E. et al., 2016. *Nature Plants*, 2: 16178. 500) to identify potential PEPC genes. All homologous protein sequences of the predicted PEPC family members were accepted if they were satisfied with expectation (E) value<1E-10. The expression data of the *Agave* PEPCs was also obtained from the *A. americana* transcriptomics data (Abraham et al. 2016). For *Agave* PEPC genes expression pattern, the log 10 transformed FPKM values and z-score normalized relative expression were used for heatmap analysis.

Phylogenetic Analysis

Multiple alignment of PEPC proteins was performed using the MAFFT online service (Katoh K. et al. 2017. *Briefings in Bioinformatics* bbx108). The maximum likelihood (ML) phylogenetic tree was constructed using W-IQ-TREE (Trifinopoulos J. et al. 2016. *Nucleic Acids Research* 44: W232-W235). Sequences used were: foxtail millet (*Setaria italica*) (AY491400), foxtail millet (*S. italica*) $C_4$ (AF495586), maize (*Zea mays*) $C_3$ (X61489), maize (*Z. mays*) $C_4$ (X15642), maize (*Z. mays*) root (AB012228), rice (*Oryza sativa*) $C_3$ (OS08g0366000, Os09g0315700, Os01g0758300), rice (*O. sativa*) root (OS02g0244700), sorghum (*Sorghum bicolor*) $C_4$ (X63756), sugarcane (*Saccharum* hybrid var. H32-8560) $C_3$ (M86661), sugarcane (*Saccharum* hybrid cultivar Taitang2) $C_4$ (AY135709), and wheat (*Triticum aestivum*) (AJ007705) (Masumoto C. et al. 2010. *PNAS*, 107: 5226-5231). The bootstrap values were calculated as percentages for 1000 replications.

Structural Modeling and Molecular Dynamics Simulation

The *A. americana* PEPC1 model was built using the iterative threading assembly refinement (I TASSER, V5.1) (Roy A. et al. 2010. *Nat Protoc*, 5: 725-738) protein structure modeling toolkit. Structure averaging from multiple MD simulations, or, a single long time-scale MD simulation, could effectively refine the predicted structures (Mirjalili V. et al. 2014. *Proteins*, 82: 196-207). Here, a 200-ns MD simulation without restraint was performed for the best model constructed by I-TASSER. The online program Mol-Probity (Chen V B. et al., 2010. *Acta Crystallogr, D* 66: 12-21) was applied to validate the rotamers of Asn, Gln and His, and to determine the protonation states of titratable residues of Glu, Asp, Lys, Arg and His. Missing hydrogen atoms were added using the HBUILD module in CHARMM (Brooks B R. 2009. *Journal of Computational Chemistry*, 30: 1545-1614). A water box with at least 15 Å to the edge of the protein was used, and sodium/chloride ions were added to balance the net charge of the whole system. The final model has 120,210 atoms with 34,893 water molecules, and has a size of 118×106×102 Å3. The MD simulations were performed using the software NAMD (Phillips J C. et al. 2005. *Journal of Computational Chemistry* 26: 1781-1802). The CHARMM protein force field (Best R B. et al., 2012. *J Chem Theory Comput*, 8: 3257-3273) and TIP3P water model (Jorgensen W L. et al. 1983. *Journal of Chemical Physics*, 79: 926-935) were adopted in all MD simulations. A time step of 2-fs was applied with the SHAKE algorithm to fix the bonds involving hydrogen atoms. After a 50,000 steps energy minimization, the temperature of the system was gradually heated to 300 K with a rate of 0.001 K per time step. The MD simulations were performed under an NPT ensemble with the system pressure of 1 atm and temperature of 300 K maintained by the Langevin piston controls. Cutoff of switching between 9 and 11 Å was applied for the non-bonded interactions, and particle mesh Ewald summation with a grid spacing of 1.35 Å were applied for long range electrostatic interactions, respectively. A 200 ns MD simulation was performed, and analysis was carried out on the last 50 ns of the MD trajectory. The online tool PDBsum (Laskowski R A. et al. 2018. *Protein Sci*, 27: 129-134) was used to plot the cartoon topology of the protein structure.

Plasmid Construction

A 2943-bp DNA fragment containing the coding sequence of AaPEPC1 (Aam080248) (Aam080248 transcribed RNA sequence is shown by SEQ ID NO: 17. Aam080248 coding sequence is shown by SEQ ID NO: 18. Aam080248 protein is shown by SEQ ID NO:19) fused to two FLAG epitope tags (Terpe K. 2003. *Applied Microbiology and Biotechnology*, 60: 523-533) was chemically synthesized by Integrated DNA Technology (Coralville, Iowa) and used to produce a chimeric gene construct, p35S:FLAG-AaPEPC1/pNOS:nptII. The vector contains the CaMV35S promoter driving FLAG-AaPEPC1 and nopaline synthase (NOS) promoter driving the nptII gene for kanamycin resistance as a selection marker. The vector was delivered into the *Agrobacterium tumefaciens* strain, GV3101, for plant transformation.

Plant Transformation

A woodland tobacco (*Nicotiana sylvestris*) was employed for genetic transformation. The generation and nursing of transgenic plants were carried out as previously described (Zhang L. et al. 2012. *In Vitro Cellular & Developmental Biology-Plant*, 48: 275-282). The transgenic lines were assumed as single copy lines with separation rate at about 3:1 (kanamycin resistance versus sensitivity) in T1 generation, and the homozygous lines were assumed if there was no separation in T2 and T3 generation (n>100).

Measurement of Photosynthesis

Photosynthetic rate, stomatal conductance and transpiration rate in the leaves of transgenic plants and WT grown in pots for 6 weeks were measured according to the methods of Liu D. et al. (2014. *Plant Cell, Tissue and Organ Culture*, 117: 1-16). Relative chlorophyll content (SPAD value in fresh leaves) was measured with Chlorophyll Meter SPAD-502 (Minolta, Japan) (Liu et al. 2014. *Plant Cell, Tissue and Organ Culture*, 117: 1-16).

Analysis of Malate, Glucose and Proline Content

Mature leaves were sampled into liquid nitrogen at the indicated times and stored at −80° C. until use. The frozen leaf samples were prepared and assayed for malate and glucose content using the standard enzyme-linked spectrophotometric methods according to the manufacturer's instructions of malate and glucose assay kit, respectively (Sigma-Aldrich, #GAHK20, #MAK067). Proline content were analyzed as described by He S. (2009. *Plant Cell, Tissue and Organ Culture*, 96: 69).

Carbon Isotope Ratio Analysis

Plants were well watered throughout the growing period. Matures leaves were harvested from 6-week-old plants and dried for 1 week at 50° C. Finely ground dry powder were placed in capsules and then analyzed at the University of California Davis Stable Isotope Facility. Carbon isotope compositions of samples are calculated as described by Winter and Holtum (Winter K. et al. 2002. *Plant Physiology*, 129: 1843-1851).

Salt and Drought Stress Treatment

For salt tolerance analysis, the transgenic plants and controls were watered with 200 mM NaCl solution every other day for 4 weeks according to the method of Liu et al. (Liu et al. 2014. *Plant Cell, Tissue and Organ Culture*, 117: 1-16). For drought tolerance analysis, the plants were subjected to progressive drought by withholding water until a nearly lethal effect of dehydration was observed on WT. Recovery study was performed for plants under drought stress by re-irrigating with tap water (Xia Z. et al. 2013. *PloS One*, 8: e69787). After salt or drought treatment, the plants were dried for 48 h in an oven at 80° C. and weighed (Liu et al. 2014. *Plant Cell, Tissue and Organ Culture*, 117: 1-16). All treatments were performed in triplicate.

Expression Analysis of the Related Genes

The expression of related genes in the transgenic plants and WT was analyzed by qRT-PCR. Specific primers designed for each are listed in Table 1. Tobacco β-actin gene was used as an internal control. Quantification of the gene expression was done with comparative CT method (Schmittgen T D. et al. 2008. *Nat Protoc*, 3: 1101-1108).

TABLE 1

Primers

| Primer name | Primer sequence (5'-3') |
| --- | --- |
| AaPEPC1_qPCR_F2 | GCCTACAGGAGGAGGAGTACGCTG (SEQ ID NO: 1) |
| AaPEPC1_qPCR_R2 | CCTGACTGACTGAGTCGGATGTGC (SEQ ID NO: 2) |
| NsyALMT_qRT_F1 | AATGGTTCAGAGTATGGATTGG (SEQ ID NO: 3) |
| NsyALMT_qRT_R1 | TAAGTGTCGCACCTATGCTG (SEQ ID NO: 4) |
| NsyCA4_qRT_F1 | GTCAAAGCCCTAAGTTCTTGGT (SEQ ID NO: 5) |
| NsyCA4_qRT_R1 | ACCCACTCTTCAATGAAATCACTG (SEQ ID NO: 6) |
| NsyMDH_qRT_F1 | TTGGATATGCTCTTGTTCCGA (SEQ ID NO: 7) |
| NsyMDH_qRT_R1 | GCAACAACACCTTTGAGAAGAG (SEQ ID NO: 8) |
| NsyME_qRT_F1 | TGGCTTGTGGATTCAAAGGG (SEQ ID NO: 9) |
| NsyME_qRT_R1 | GGTTGGCTTAATGGTCTTAACAG (SEQ ID NO: 10) |
| NsyP5CR_qRT_F1 | TAATACTCAGGTGGTTGAAGACAG (SEQ ID NO: 11) |
| NsyP5CR_qRT_R1 | CAAAGTAAAGACAGTGGCGG (SEQ ID NO: 12) |
| NsyP5CS1_qRT_F1 | CTTCAGGCACTTTCTTCCCA (SEQ ID NO: 13) |
| NsyP5CS1_qRT_R1 | CATCAGCAACCTCCGTTCTC (SEQ ID NO: 14) |
| NsyTDT_qRT_F1 | TGGAACTGTTAGTGTCATGATGG (SEQ ID NO: 15) |
| NsyTDT_qRT_R1 | CTGGTGCAATGGCTAAGTATGG (SEQ ID NO: 16) |

Statistical Analysis

The data presented as the mean±SD were analyzed by one-way ANOVA analysis with post-hoc Tukey honestly significant difference (HSD). A p-value of <0.05 was considered to be statistically significant.

What is claimed is:

1. A method comprising:
   (i) introducing into a $C_3$ or $C_4$ plant cell a nucleic acid encoding a crassulacean acid metabolism (CAM)-specific phosphoenolpyruvate carboxylase (CAM-PEPC) from *Agave Americana*,
   (ii) producing a C3 or C4 plant from the plant cell and expressing the CAM-PEPC in the plant, wherein the CAM-PEPC is the only CAM-specific protein expressed in the plant, wherein expression of the CAM-PEPC improves resistance to drought and high salt in the plant as compared to a C3 or C4 plant without the expression of a CAM-PEPC, and
   (iii) growing the plant under conditions that include a period of drought or high salt.

2. The method of claim 1, wherein the CAM-PEPC comprises an amino acid sequence substantially identical to SEQ ID NO: 19.

3. The method of claim 1, wherein the nucleic acid comprises a nucleic acid sequence substantially identical to SEQ ID NO: 18.

4. The method of claim 1, wherein the plant cell is from a $C_3$ plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

5. The method of claim 1, wherein the plant cell is from a $C_4$ plant selected from the group consisting of genera *Panicum, Saccharum, Setaria, Sorghum* and *Zea*.

6. The method of claim 1, wherein the plant is grown in an arid environment or a semiarid environment.

7. The method of claim 1, wherein the nucleic acid comprises a promoter selected from the group consisting of a constitutive promoter, a tissue-specific promoter, and a regulated promoter.

8. The method of claim 7, wherein the promoter is a leaf-specific promoter selected from the group consisting of a ribulose-1,5-bisphosphate carboxylase/oxygenase (RbcS) promoter, a chlorophyll a/b binding-6 (cab6) promoter, a chlorophyll a/b binding-1(Cab-1) promoter, a cab IR promoter from rice, a pyruvate orthophosphate dikinase (PPDK) promoter, a light-harvesting complex of photosystem (Lhcb1*2) promoter, a sucrose-H+ symporter (SUC2) promoter and a thylakoid membrane protein promoter.

9. The method of claim 7, wherein the promoter is a constitutive promoter selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

10. The method of claim 7, wherein the promoter is a regulated promoter selected from the group consisting of a stress induced promoter, a chemical-induced promoter, a light induced promoter, a dark-induced promoter, and a circadian-clock controlled promoter.

11. The method of claim 1, wherein the CAM-PEPC comprises an amino acid sequence of SEQ ID NO: 19.

12. The method of claim 1, wherein the nucleic acid comprises a nucleic acid sequence of SEQ ID NO: 18.

13. A method of producing increased biomass under conditions that include a period of drought or high salt comprising: (i) providing a $C_3$ or $C_4$ plant engineered to express a nucleic acid encoding a crassulacean acid metabolism (CAM)-specific phosphoenolpyruvate carboxylase (CAM-PEPC) from *Agave Americana*, wherein the CAM-PEPC is the only CAM-specific protein expressed in the plant cell wherein expression of the CAM-PEPC improves resistance to drought and high salt in the plant as compared to a C3 or C4 plant without the expression of a CAM-PEPC; and (ii) growing the plant under conditions that comprise conditions that include a period of drought or high salt; (iii) harvesting the plant expressing the CAM-PEPC to acquire the increased biomass.

14. The method of claim 13, wherein the CAM-PEPC comprises an amino acid sequence substantially identical to SEQ ID NO: 19.

15. The method of claim 13, wherein the nucleic acid comprises a nucleic acid sequence substantially identical to SEQ ID NO: 18.

16. The method of claim 13, wherein the CAM-PEPC comprises an amino acid sequence of SEQ ID NO: 19.

17. The method of claim 13, wherein the nucleic acid comprises a nucleic acid sequence of SEQ ID NO: 18.

18. The method of claim 13, wherein the plant is a $C_3$ plant selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

19. The method of claim 13, wherein the plant is a $C_4$ plant selected from the group consisting of genera *Panicum, Saccharum, Setaria, Sorghum* and *Zea*.

20. The method of claim 13, wherein the plant is grown in an arid environment or a semiarid environment.

21. The method of claim 13, wherein the nucleic acid comprises a promoter selected from the group consisting of a constitutive promoter, a tissue-specific promoter, and a regulated promoter.

22. The method of claim 21, wherein the promoter is a leaf-specific promoter selected from the group consisting of a ribulose-1,5-bisphosphate carboxylase/oxygenase (RbcS) promoter, a chlorophyll a/b binding-6 (cab6) promoter, a chlorophyll a/b binding-1(Cab-1) promoter, a cab IR promoter from rice, a pyruvate orthophosphate dikinase (PPDK) promoter, a light-harvesting complex of photosystem (Lhcb1*2) promoter, a sucrose-H+ symporter (SUC2) promoter and a thylakoid membrane protein promoter.

23. The method of claim 21, wherein the promoter is a constitutive promoter selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

24. The method of claim 21, wherein the promoter is a regulated promoter selected from the group consisting of a stress induced promoter, a chemical-induced promoter, a light induced promoter, a dark-induced promoter, and a circadian-clock controlled promoter.

* * * * *